United States Patent [19]
Lal et al.

[11] Patent Number: 6,063,596
[45] Date of Patent: May 16, 2000

[54] G-PROTEIN COUPLED RECEPTORS ASSOCIATED WITH IMMUNE RESPONSE

[75] Inventors: Preeti Lal, Santa Clara; Olga Bandman; Jennifer L. Hillman, both of Mountain View; Henry Yue, Sunnyvale, all of Calif.

[73] Assignee: Incyte Pharmaceuticals, Inc., Palo Alto, Calif.

[21] Appl. No.: 08/988,876

[22] Filed: Dec. 11, 1997

[51] Int. Cl.[7] .................................. C12N 1/21; C12N 5/10; C12N 15/12

[52] U.S. Cl. ............................... 435/69.1; 435/6; 435/7.1; 435/7.2; 435/252.3; 435/320.1; 536/23.5

[58] Field of Search .................................. 435/69.1, 69.7, 435/252.3, 320.1, 6, 71, 72; 536/23.4, 23.5

[56] References Cited

FOREIGN PATENT DOCUMENTS

WO96/39511A 12/1996 WIPO.

OTHER PUBLICATIONS

Database EMBL, ID HSA42813, Accession No. AA042813, Sep. 7, 1996, XP002100507.
Database EMBL, ID AA626037, Accession No. AA626037, Oct. 28, 1997, XP002100508.
Database EMBL, ID HS920360, Accession No. W79920, Jun. 27, 1996, XP00210059.
Database EMBL, ID HS123364, Accession No. W79123, Jun. 27, 1996, XP002100510.
Watson, S. and S. Arkinstall, *The G–Protein Linked Receptor Facts Book*, Academic Press, San Diego, CA, pp. 2–7 (1994).
Bolander, F.F., *Molecular Endocrinology*, Academic Press, San Diego, CA, pp. 162–176 (1994).
Parmentier, M. et al., "Expression of members of the putative olfactory receptor gene family in mammalian germ cells", *Nature*, 355: 453–455 (1992).
Buck, L. and R. Axel, "A Novel Multigene Family May Encode Odorant Receptors: A Molecular Basis for Odor Recognition", *Cell*, 65: 175–187 (1991).
Crowe, M.L. et al., "Olfactory receptor–encoding genes and pseudogenes are expressed in humans", *Gene*, 169: 247–249 (1996).
Nomura, N. et al., "Prediction of the Coding Sequences of Unidentified Human Genes. II. The Coding Sequences of 40 New Genes (KIAA0041–KIAA0080) Deduced by Analysis of cDNA Clones from Human Cell Line KG–1 (Supplement)", *DNA Res.*, 1: 251–262 (1994).
Charlton, M.E. et al., "The isolation and characterization of a novel G protein–coupled receptor regulated by immunologic challenge", *Brain Res.*, 764: 141–148 (1997).
Issel–Tarver, L. and J. Rine, (Direct Submission), GenBank Sequence Database (Accession 1314667), National Center for Biotechnology Information, National Library on Medicine, Bethesda, Maryland, 20894, (GI 1314667).
Issel–Tarver, L. and J. Rine, "Organization and expression of canine olfactory receptor genes", *Proc. Natl. Acad. Sci. USA*, 93: 10897–10902 (1996).
Buck, L. and R. Axel, (Direct Submission), GenBank Sequence Database (Accession 205814), National Center for Biotechnology Information, National Library of Medicine, Bethesda, Maryland, 20894, (GI 205814).
Parmentier, M., (Direct Submission), GenBank Sequence Database (Accession 32086), National Center for Biotechnology Information, National Library of Medicine, Bethesda, Maryland, 20894, (GI 32086).
Nomura, N., (Direct Submission), GenBank Sequence Database (Accession 285995), National Center for Biotechnology Information, National Library of Medicine, Bethesda, Maryland, 20894, (GI 49443).
Honda, Z., (Direct Submission), GenBank Sequence Database (Accession 49443), National Center for Biotechnology Information, National Library of Medicine, Bethesda, Maryland, 20894, (GI 871359).
Erb, L. et al., "Functional expression and phtoaffinity labeling of a cloned $P_{2U}$ purinergic receptor", *Proc. Natl. Acad. Sci. USA*, 90: 10449–10453 (1993).

*Primary Examiner*—John Ulm
*Attorney, Agent, or Firm*—Colette C. Muenzen; Incyte Pharmaceuticals, Inc.

[57] ABSTRACT

The invention provides two human G-protein coupled receptors associated with immune response (GRIR) and polynucleotides which identify and encode GRIR. The invention also provides expression vectors, host cells, antibodies, agonists, and antagonists. The invention also provides methods for treating or preventing disorders associated with expression of GRIR.

12 Claims, 15 Drawing Sheets

FIGURE 1A

```
                9        18        27        36        45        54
5' GGC CAG GAC GGT GTC GAT CTC CTA ACC CCG TGA TCT GCC CTC AGC CTC CCA 63        72        81        90        99        108
GAG TGC TGG GAC TAC AGG CGT GAG CCA CCG CAT CTG GCC AAA CTT TCT GAT GAA 117       126       135       144       153       162
AAC TCT AAG TCC ACC TAA GCT AAG GAC AGG AGT TAC AGC TTC CAT GAA TTT TAA 171       180       189       198       207       216
AAC CAG ACC CAC CGA TTT GAG TAA GCA ATT ACT CTC TTG AAG GAG AAA AGT CAG 225       234       243       252       261       270
AAA ACA TAA TGA TGA AAT CAC TAG GAC CTA ACT GGC ATG TGG AAT TAT TTT CTG 279       288       297       306       315       324
CTT ATG AAC TAT CAA CTT TAA TTT CAT TTC CAG ATG ACA TGG TCT CAG CTG TTC 333       342       351       360       369       378
TAC AGT GTT TAT AAA TGT TCT AAA TCA AGG GAA TTC ATC AAT CTA GTA GAA TAA 387       396       405       414       423       432
AAT ATT TGA GTT CTT AAT TTC CTT TAA TTA GGA TAA CCT TTT TCT TCA AGT GAA 441       450       459       468       477       486
GAG AAT GGT TTT ATT ACA TAG TTT TCT TCG GAA AAG ATA GGC TGT ATT TTC TAG
```

```
     495         504         513         522         531         540
CAG TTA CGA ATT TGT TAT GTA TGA TCT GGT TCT TGG AAC ATT CTT GAA TCT 549         558         567         576         585         594
AGT GTC TCT AAG GCA GGT GTG TAC AGC AAG AAG TGA ATA ACA CAG AAA TCA ATG 603         612         621         630         639         648
ATG AAA GCA TTA GAA GAC AAT TGA GTC TGT CAG AAC TGC AAA ATA TTG CTG AGT 657         666         675         684         693         702
GTG GAT TGC TCT GAA ATC TGA AAA CAT TAC TTG TGA ATT GCT TCT ATT CAA AAT 711         720         729         738         747         756
GCA GAC ACA ATG CCA GGT GTT GGT TTA CTT GTT TCC CAT TTT TCA ACC CTC GTT
        M   P   G   V   G   L   L   V   S   H   F   S   T   L   V 765         774         783         792         801         810
TCT AGG CAA AGG TGT CCA AAT TAT GCA GAC CCA CAG AAT CTA ACA GAT GTC TCT
S   R   Q   R   C   P   N   Y   A   D   P   Q   N   L   T   D   V   S 819         828         837         846         855         864
ATA TTC CTC CTC CTA GAA GTC TCA GGG GAT CCA GAA CTG CAG CCA GTC CTT GCT
I   F   L   L   L   E   V   S   G   D   P   E   L   Q   P   V   L   A
```

FIGURE 1B

```
                873      882      891      900      909      918
GGG CTG TTC CTG TCC ATG TGC CTG GTC ACG GTG CTG GGG AAC CTG CTC ATC ATC
 G   L   F   L   S   M   C   L   V   T   V   L   G   N   L   L   I   I 927      936      945      954      963      972
CTG GCC ATC AGC CCT GAC TCC CAC CTC CAC ACC CCC ATG TAC TTC TTC CTC TCC
 L   A   I   S   P   D   S   H   L   H   T   P   M   Y   F   F   L   S 981      990      999     1008     1017     1026
AAC CTG TCC TTG CCT GAC ATC GGT TTC ACC TCC ACC GTC CCC AAG ATG ATT
 N   L   S   L   P   D   I   G   F   T   S   T   T   V   P   K   M   I 1035     1044     1053     1062     1071     1080
GTG GAC ATC CAG TCT CAC AGC AGA GTC ATC TCC TAT GCA GGC TGC CTG ACT CAG
 V   D   I   Q   S   H   S   R   V   I   S   Y   A   G   C   L   T   Q 1089     1098     1107     1116     1125     1134
ATG TCT CTC TTT GCC ATT TTT GGA GGC ATG GAA GAG AGA CAT GCT CCT GAG TGT
 M   S   L   F   A   I   F   G   G   M   E   E   R   H   A   P   E   C 1143     1152     1161     1170     1179     1188
GAT GGC CTA TGA CTG GTT TGT AGC CAT CTG TCA CCC GCT ATA TCA TTC ACC ATC
 D   G   L   *   L   V   C   S   H   L   S   P   A   I   S   F   T   I
```

FIGURE 1C

```
       1197        1206             1215        1224             1233        1242
ATG AAC CCG TGT TTC TGT GCC TTT CTA GTT TTG TCT TTT TTT CTC AGT
 M   N   P   C   F   C   A   F   L   V   L   S   F   F   L   S 1251        1260             1269        1278             1287        1296
CTT TTA GAC TCC CAG CTG CAC AAC TTG ATT GCC TTA CAA GTG ACC TGC TTC AAG
 L   L   D   S   Q   L   H   N   L   I   A   L   Q   V   T   C   F   K 1305        1314             1323        1332             1341        1350
GAT GTG GAA ATT CCT AAT TTC TTC TGT GAC CCT TCT CAA CTC TCC CAT CTT GCA
 D   V   E   I   P   N   F   F   C   D   P   S   Q   L   S   H   L   A 1359        1368             1377        1386             1395        1404
TGT TGT GAC ACC TTC ACC ATT AAC ATA ATC ATG TAT TTC CCT GCT GCC ATA TTT
 C   C   D   T   F   T   I   N   I   I   M   Y   F   P   A   A   I   F 1413        1422             1431        1440             1449        1458
GGT TTT CTT CCC ATC TCA GGG ACC TTT TCT CTT ACT GTA AAA ATT CTT TCC TCC
 G   F   L   P   I   S   G   T   F   S   L   T   V   K   I   L   S   S 1467        1476             1485        1494             1503        1512
ATT CTG AGG GTT TCA TCA TCA GGT GGG AAG TAT GGG AAA CCT TCT CCA CCT GTG GGT
 I   L   R   V   S   S   S   G   G   K   Y   G   K   P   S   P   P   V   G
```

FIGURE 1D

```
      1521              1530              1539         1548              1557         1566
CTC ACC TGT CAG TTG TTT GCT GGA GGG TAC CTC GGT TCA GAT GTG TCA TCT TCC
 L   T   C   Q   L   F   A   G   G   Y   L   G   S   D   V   S   S   S 1575              1584              1593         1602              1611         1620
CCG AGA AAG AGT GCA GTG GCC TCA GTG ATG TAC ACG GTG GTC ACC CCC ATG CTG
 P   R   K   S   A   V   A   S   V   M   Y   T   V   V   T   P   M   L 1629              1638              1647         1656              1665         1674
AAC CCC TTC ATG TAC AGC CTG AGA AAC AGG GAT ATG AAA AGT GTC CTG CGG CGG
 N   P   F   M   Y   S   L   R   N   R   D   M   K   S   V   L   R   R 1683              1692              1701         1710              1719         1728
CCG CAC AGC ACA GTC TAA TCT CAA TAT CTT CTT ATC TGT TCC ATT CCT TTT
 P   H   S   T   V 1737              1746              1755         1764              1773         1782
GTA GTG TGG GTT AAA AAA GGC AAG ATC AAA TAA GAT TGA TCT CAG GAC CTG 1791              1800              1809         1818              1827
AAC ACT CAT GTT TGT ATA CGA CCC ACA AGT AGT CCC CGG AGG CCC G 3'
```

| | | | |
|---|---|---|---|
| 238 | T F S L T V K I L S S I L R V S S S G G K Y K P - - - - S P P V G L T C Q L F A | 364702 |
| 214 | V L Y S Y F K I V S S I R G I S S A H S K Y K A F S T C A S H L S V V S L F Y C | g1314667 |
| 214 | I F Y S Y F K I V S S I C A I S S V H G K Y K A F S T C A S H L S V V S L F Y C | g205814 |
| 214 | I L G S Y A R I V S S I L K V P S S K G I C K A F S T C G S H L S V V S L F Y G | g32086 |
| | | | |
| 274 | - - G G Y L G S D V S S S P R K S A V A S V M Y T V V T P M L N P F M Y S L R | 364702 |
| 254 | T S L G V Y L S S A A P Q S T H T S S V A A S V M Y T V V T P M L N P F I Y S L R | g1314667 |
| 254 | T G L G V Y L S S A A N N S Q A S A T A S V M Y T V V T P M L N P F I Y S L R | g205814 |
| 254 | T V I G L Y L C S A N S S T L K D T V M A M M Y T V V T P M L N P F I Y S L R | g32086 |
| | | | |
| 311 | N R D M K S V L R R P H G S T V | 364702 |
| 294 | N K D I K G A L N V - - - F F R G K P | g1314667 |
| 294 | N K D V K S V L K K T L C E E V I R S P P S L L H F F L V L C H L P C F I F C Y | g205814 |
| 294 | N R D M K G A L S R - - - V I H Q K K T F - - - - - - - - - - - - - - - F S L | g32086 |

FIGURE 2B

```
                        9           18          27          36          45          54
5' GGA GAA TTT GAA AGG GTG CCC CAA AGG ACA ATC TCT AAA GGG GTA AGG GGG ATA 63          72          81          90          99         108
   CCT ACC TTG TCT GGT AGG GGA GAT GTT TCG TTT TCA TGC TTT ACC AGA AAA TCC 117         126         135         144         153         162
   ACT TCC CTG CCG ACC TTA GTT TCA AAG CTT CTT ATT AAT TAG AGA CAA GAA ACC 171         180         189         198         207         216
   TGT TTC AAC TTG AAG ACA CCG TAT GAG GTG AAT GGA CAG CCA GCC ACC ACA ATG 225         234         243         252         261         270
   AAA GAA ATC AAA CCA GGA ATA ACC TAT GCT GAA CCC ACG CCT CAA TCG TCC CCA 279         288         297         306         315         324
   AGT GTT TCC TGA CAC GCA TCT TTG CTT ACA GTG CAT CAC AAC TGA AGA ATG GGG
                                                                         M   G 333         342         351         360         369         378
   TTC AAC TTG ACG CTT GCA AAA TTA CCA AAT AAC GAG CTG CAC GGC CAA GAG AGT
    F   N   L   T   L   A   K   L   P   N   N   E   L   H   G   Q   E   S 387         396         405         414         423         432
   CAC AAT TCA GGC AAC AGG AGC GAC GGG CCA GGA AAG AAC ACC CTT CAC AAT
    H   N   S   G   N   R   S   D   G   P   G   K   N   T   L   H   N

FIGURE 3A
```

```
      441            450            459            468            477            486
GAA TTT GAC ACA ATT GTC TTG CCG GTG CTT TAT CTC ATT ATA TTT GTG GCA AGC
 E   F   D   T   I   V   L   P   V   L   Y   L   I   I   F   V   A   S 495            504            513            522            531            540
ATC TTG CTG AAT GGT TTA GCA GTG TGG ATC TTC TTC CAC ATT AGG AAT AAA ACC
 I   L   L   N   G   L   A   V   W   I   F   F   H   I   R   N   K   T 549            558            567            576            585            594
AGC TTC ATA TTC TAT CTC AAA AAC ATA GTG GTT GCA GAC CTC ATA ATG ACG CTG
 S   F   I   F   Y   L   K   N   I   V   V   A   D   L   I   M   T   L 603            612            621            630            639            648
ACA TTT CCA TTT CGA ATA GTC CAT GAT GCA GGA TTT GGA CCT TGG TAC TTC AAG
 T   F   P   F   R   I   V   H   D   A   G   F   G   P   W   Y   F   K 657            666            675            684            693            702
TTT ATT CTC TGC AGA TAC ACT TCA GTT TTG TTT TAT GCA AAC ATG TAT ACT TCC
 F   I   L   C   R   Y   T   S   V   L   F   Y   A   N   M   Y   T   S 711            720            729            738            747            756
ATC GTG TTC CTT GGG CTG ATA AGC ATT GAT CGC TAT CTG AAG GTG GTC AAG CCA
 I   V   F   L   G   L   I   S   I   D   R   Y   L   K   V   V   K   P
```

FIGURE 3B

```
       765         774         783         792         801         810
TTT GGG GAC TCT CGG ATG TAC AGC ATA ACC TTC ACG AAG GTT TTA TCT GTT TGT
 F   G   D   S   R   M   Y   S   I   T   F   T   K   V   L   S   V   C 819         828         837         846         855         864
GTT TGG GTG ATC ATG GCT GTT TTG TCT TTG CCA AAC ATC CTG ACA AAT GGT
 V   W   V   I   M   A   V   L   S   L   P   N   I   L   T   N   G 873         882         891         900         909         918
CAG CCA ACA GAG GAC AAT ATC CAT GAC TGC TCA AAA CTT AAA AGT CCT TTG GGG
 Q   P   T   E   D   N   I   H   D   C   S   K   L   K   S   P   L   G 927         936         945         954         963         972
GTC AAA TGG CAT ACG GCA GTC ACC TAT GTG AAC AGC TGC TTG TTT GTG GCC GTG
 V   K   W   H   T   A   V   T   Y   V   N   S   C   L   F   V   A   V 981         990         999         1008        1017        1026
CTG GTG ATT CTG ATC GGA TGT TAC ATA GCC ATA TCC AGG TAC ATC CAC AAA TCC
 L   V   I   L   I   G   C   Y   I   A   I   S   R   Y   I   H   K   S 1035        1044        1053        1062        1071        1080
AGC AGG CAA TTC ATA AGT CAG TCA AGC CGA AAG CGA AAA CAT AAC CAG AGC ATC
 S   R   Q   F   I   S   Q   S   S   R   K   R   K   H   N   Q   S   I
```

FIGURE 3C

```
          1089            1098            1107            1116            1125            1134
AGG GTT GTT GTG GCT GTG TAT TTT ACC TGC TTT CTA CCA TAT CAC TTG TGC AGA
 R   V   V   V   A   V   Y   F   T   C   F   L   P   Y   H   L   C   R 1143            1152            1161            1170            1179            1188
ATG CCT TCT ACT TTT AGT CAC TTA GAC AGG CTT TTA GAT GAA TCT GCA CAA AAA
 M   P   S   T   F   S   H   L   D   R   L   L   D   E   S   A   Q   K 1197            1206            1215            1224            1233            1242
ATC CTA TAT TAC TGC AAA GAA ATT ACA CTT TTC TTG TCT GCG TGT AAT GTT TGC
 I   L   Y   Y   C   K   E   I   T   L   F   L   S   A   C   N   V   C 1251            1260            1269            1278            1287            1296
CTG GAT CCA ATA ATT TAC TTT TTC ATG TGT AGG TCA TTT TCA AGA TGG CTG TTC
 L   D   P   I   I   Y   F   F   M   C   R   S   F   S   R   W   L   F 1305            1314            1323            1332            1341            1350
AAA AAA TCA AAT ATC AGA CCC AGG AGT GAA AGC ATC AGA TCA CTG CAA AGT GTG
 K   K   S   N   I   R   P   R   S   E   S   I   R   S   L   Q   S   V 1359            1368            1377            1386            1395            1404
AGA AGA TCG GAA GTT CGC ATA TAT TAT GAT TAC ACT GAT GTG TAG GCC TTT TAT
 R   R   S   E   V   R   I   Y   Y   D   Y   T   D   V   *   A   F   Y 1413            1422            1431            1440
TGT TTG TTG GAA TCG ATA TGT ACA AAG TGT AAT ACA TCA G
```

FIGURE 3D

```
1   MGFNLTLAKLPNNELHGQESHNSGNRSDGPGKNTTLHNEF   1650519
1   M------------------------INSTSTQPPDESCSQNLLI   g285995
1   MELN---------------------------SSSRVDSEF   g49443

41  DTIVLPVLYLIIFVASILLNGLAVWIF------FHIRNKTSFI   1650519
21  TQQIIPVLYCMVFIAGILLNGVSGWIF------EYVPSSKSFI   g285995
14  RYTLFPIVYSIIFVLGIIANGYVLWVEARLYPSKKLNEIK    g49443

78  FYLKNIVVADLIMTLTFPFRIVHDAGFGPWYFKFILCRYT    1650519
58  IYLKNIVIADFVMSLTFPFKILGDSGLGPWQLNVFVCRVS    g285995
54  IFMVNLTVADLLFLITLPLWIVYYSNQGNWFLPKFLCNLA    g49443

118 SVLFYANMYTSIVFLGLIISIDRYLKVVKPFGDSRMYSITF    1650519
98  AVLFYVNMYVSIVFFEGLISFDRYYKIIVKPLWTSFIQSVSY   g285995
94  GCLFFINTYCSVAFLGVITYNRFQAVKYPIKTAQATTRKR    g49443

158 TKVLSVCVWVIMA-----VLSLPNIILTNGQPTEDNIHDC    1650519
138 SKLLSVIVWMLML-----LLAVPNILTNQSVREVTQIKC     g285995
134 GIALSLVIWVAIVAAASYFLVMDSTNVVSNKAGSGNITRC    g49443
```

| LIBRARY | CLONES | TISSUE DESCRIPTION |
|---|---|---|
| Gastrointestinal | | |
| COLNNOT16 | 2 | colon, sigmoid, 62 M, match to COLNTUT03 |
| COLNTUT03 | 1 | colon tumor, 62 M, match to COLNNOT16 |
| EPIGNOT01 | 1 | epiglotus |
| GBLANOT02 | 1 | gallbladder, 21 M |
| PANCNOT15 | 1 | pancreas, islet cell hyperplasia, 15 M |
| PANCNOT01 | 1 | pancreas, 29 M |
| SINIUCT01 | 1 | small intestine, ileum, 42 M |
| SININOT04 | 1 | small intestine, ileum, Crohn's, 26 M |
| Male reproductive | | |
| PROSNOT19 | 1 | prostate, 59 M |
| PROSNOT01 | 1 | prostate, 78 M |
| TESTNOT03 | 2 | testis, 37 M |
| Muscle | | |
| MUSCNOT07 | 1 | muscle, forearm, 38 F |
| LVENNOT03 | 1 | heart, left ventricle, 31 M |
| HEARNOT06 | 1 | heart, 44 M |
| Other | | |
| BLADTUT05 | 1 | bladder tumor, 66 M, match to BLADNOT06 |
| KIDNFET01 | 2 | kidney, fetal, F |
| BRSTTUT01 | 1 | breast tumor, 55 F, match to BRSTNOT02 |
| BRSTNOT23 | 1 | |
| KERANOT02 | 1 | keratinocytes, primary cell line, 30 F |
| LUNGTUT03 | 1 | lung tumor, 69 M, match to LUNGNOT15 |
| BRAITUT13 | 1 | brain tumor, meningioma, 68 M |

FIGURE 5A

| LIBRARY | CLONES | TISSUE DESCRIPTION |
|---|---|---|
| Reproductive | | |
| PROSTUT09 | 2 | prostate tumor, 66 M |
| PENITUT01 | 1 | penis tumor, carcinoma, 64 M |
| PENGNOT01 | 1 | penis, glans tissue removed along with neoplasm |
| OVARTUT04 | 2 | ovarian tumor, 53 F |
| Other | | |
| NPOLNOT01 | 1 | nasal polyp, 78 M |
| BLADNOT06 | 1 | bladder, 66 M, match to BLADTUT05 |

FIGURE 5B

G-PROTEIN COUPLED RECEPTORS ASSOCIATED WITH IMMUNE RESPONSE

FIELD OF THE INVENTION

This invention relates to nucleic acid and amino acid sequences of two new G-protein coupled receptors associated with immune response and to the use of these sequences in the diagnosis, treatment, and prevention of diseases associated with cell proliferation and cell signaling.

BACKGROUND OF THE INVENTION

G-protein coupled receptors (GPCR) are a superfamily of integral membrane proteins which transduce extracellular signals. GPCRs include receptors for biogenic amines, e.g., dopamine, epinephrine, histamine, glutamate (metabotropic effect), acetylcholine (muscarinic effect), and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and thrombin; and for sensory signal mediators, e.g., retinal photopigments and olfactory stimulatory molecules.

The structure of these highly-conserved receptors consists of seven hydrophobic transmembrane regions, cysteine disulfide bridges between the second and third extracellular loops, an extracellular N-terminus, and a cytoplasmic C-terminus. Three extracellular loops alternate with three intracellular loops to link the seven transmembrane regions. The N-terminus interacts with ligands, the disulfide bridge interacts with agonists and antagonists, and the large third intracellular loop interacts with G proteins to activate second messengers such as cyclic AMP, phospholipase C, inositol triphosphate, or ion channel proteins. The most conserved parts of these proteins are the transmembrane regions and the first two cytoplasmic loops. A conserved, acidic-Arg-aromatic triplet present in the second cytoplasmic loop may interact with the G proteins. Most members belongs to this superfamily contain a characteristic consensus pattern. (Watson, S. and S. Arkinstall (1994) *The G-protein Linked Receptor Facts Book*, Academic Press, San Diego, Calif.; Bolander, F. F. (1994) *Molecular Endocrinology*, Academic Press, San Diego, Calif.)

Odorant receptors are members of a multigene family primarily responsible for transmission of volatile chemical signals from the environment through the olfactory neuron to cortical regions of the brain. Odorant receptors have been detected in olfactory epithelium of many mammalian species (e.g., dog, rat, mouse, and human), and a homologous family of receptors is expressed in human testes where it is responsible for sperm chemotaxis. (Parmentier, M. et al. (1992; Nature 355:453–455.)

The rat olfactory protein is a member of the odorant receptor family, and one of the first molecules to be used to investigate the molecular basis of odor recognition. (Buck L. and R. Axel (1991) Cell 65:175–187.) The rat protein is 333 amino acids in length and has a glycosylation site at $N_5$, a palmitoylation site at $C_{306}$, and disulfide bonds at $C_{97}$ and $C_{189}$. Homologous human olfactory receptors (OR) and OR pseudogenes have been cloned from mRNA and genomic DNA (Crowe, M. L. (1996) Gene 169:247–249).

Chemotactic receptors are important in immune responses. They are activated by chemokines, platelet activating factor (PAF), and proteases. These receptors are found on monocytes, lymphocytes, neutrophils, basophils, eosinophils, platelets and leukocytes of several mammalian species including guinea pig, rat, mouse, and human. Chemotactic receptors are widely expressed in peripheral tissues and are present in smooth muscle, lung, brain, liver, and endothelial cells.

Complement is produced in the liver, circulates in the blood and extracellular fluid, and stimulates cells to fight infections. Complement 5 (C5) is proteolytically cleaved to produce C5a and C5b whenever the complement system is activated. C5a is one of 13 plasma proteins responsible for clearing foreign particles and organisms from the blood. In addition, human C5a, a 74 amino acid peptide, functions as a chemoattractant for immune system cells.

The C5a receptor is a GPCR which is present on neutrophils, macrophages, and mast cells and is believed to interact with a Gq-/G11-protein to activate the phosphoinositol signaling pathway. The KIAA0001/C5a receptor is 338 amino acids long and has a N-glycosylation site at Asn3. (Nomura, N. et al. (1994) DNA Res. 1:27–35.)

Chariton, M. E. et al. (1997; Brain Res. 764:141–8) identified VTR 15–20, a GPCR of 305 amino acids from rat ventral tegmentum. The cDNA shares homology to several orphan receptors, and the deduced protein demonstrates the specific regions conserved among the superfamily. VTR 15–20 is expressed throughout the mammalian nervous system and in cultured rat microglia and astrocytes. The highest levels of VTR 15–20 mRNA expression were detected in peripheral tissues and spleen. Based on cellular distribution, expression in brain and spleen, and regulation as the result of immune challenge and neuronal insult, VTR 15–20 appears to play a role in neuroimmune function.

The discovery of new G-protein coupled receptors associated with immune response and the polynucleotides encoding these receptors satisfies a need in the art by providing new compositions which are useful in the diagnosis, treatment, and prevention of diseases associated with cell proliferation and cell signaling.

SUMMARY OF THE INVENTION

The invention features substantially purified polypeptides, G-protein coupled receptors associated with immune response, referred to collectively as "GRIR" and individually as "GRIR-1" and "GRIR-2." In one aspect, the invention provides a substantially purified polypeptide, GRIR, comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant of GRIR having at least 90% amino acid identity to the amino acid sequences of SEQ ID NO:1 or SEQ ID NO:3, or to a fragment of either of these sequences. The invention also provides an isolated and purified polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3. The invention also includes an isolated and purified polynucleotide variant having at least 90% polynucleotide identity to the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides a composition comprising a polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3. The invention further provides an isolated and purified polynucleotide sequence which hybridizes under stringent conditions to the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide sequence which is complementary to the polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide sequence comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% polynucleotide identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide sequence which is complementary to the polynucleotide sequence comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence of SEQ ID NO:1, SEQ ID NO:3, a fragment of SEQ ID NO:1, or a fragment of SEQ ID NO:3, the method comprising the steps of: (a) culturing the host cell containing an expression vector containing at least a fragment of a polynucleotide sequence encoding GRIR under conditions suitable for the expression of the polypeptide; and (b) recovering the polypeptide from the host cell culture.

The invention also provides a pharmaceutical composition comprising a substantially purified GRIR having the amino acid sequence of SEQ ID NO:1, SEQ ID NO:3, a fragment of SEQ ID NO:1, or a fragment of SEQ ID NO:3 in conjunction with a suitable pharmaceutical carrier.

The invention further includes a purified antibody which binds to a polypeptide comprising the amino acid sequence of SEQ ID NO:1, SEQ ID NO:3, a fragment of SEQ ID NO:1, or a fragment of SEQ ID NO:3, as well as a purified agonist and a purified antagonist to the polypeptide.

The invention also provides a method for treating or preventing a neoplastic disorder, the method comprising administering to a subject in need of such treatment an effective amount of an antagonist of GRIR.

The invention further provides a method for treating or preventing an immune response, the method comprising administering to a subject in need of such treatment an effective amount of an antagonist of GRIR.

The invention also provides a method for detecting a polynucleotide encoding GRIR in a biological sample containing nucleic acids, the method comprising the steps of: (a) hybridizing the complement of the polynucleotide sequence encoding the polypeptide comprising SEQ ID NO:1, SEQ ID NO:3, a fragment of SEQ ID NO:1, or a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding GRIR in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of GRIR-1. The alignment was produced using MACDNASIS PRO software (Hitachi Software Engineering Co. Ltd. San Bruno, Calif.).

FIGS. 2A and 2B show the amino acid sequence alignments among GRIR-1 (364702; SEQ ID NO:1) and canine, rat and human olfactory receptors (g1314667, SEQ ID NO:5; g205814, SEQ ID NO:6; and g32086, SEQ ID NO:7, respectively).

FIGS. 3A, 3B, 3C, and 3D show the amino acid sequence (SEQ ID NO:3) and nucleic acid sequence (SEQ ID NO:4) of GRIR-2. The alignment was produced using MACDNASIS PRO software.

FIGS. 4A and 4B show the amino acid sequence alignments among GRIR-2 (1650519; SEQ ID NO:3), human KIAA0001 (g285995, SEQ ID NO:8); and rat VTR 15–20 receptor (g49443, SEQ ID NO:9).

FIGS. 5A and 5B show the northern analyses for GRIR-1 (SEQ ID NO:1) and GRIR-2 (SEQ ID NO:3) respectively.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"GRIR," as used herein, refers to the amino acid sequences of substantially purified GRIR obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to GRIR, increases or prolongs the duration of the effect of GRIR. Agonists may include proteins, nucleic acids, carbohydrates, or any other molecules which bind to and modulate the effect of GRIR.

An "allele" or an "allelic sequence," as these terms are used herein, is an alternative form of the gene encoding GRIR. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding GRIR, as described herein, include those sequences with deletions, insertions, or substitutions of different nucleotides, resulting in a polynucleotide the same GRIR or a polypeptide with at least one functional characteristic of GRIR. Included within this definition are polymorphisms which may or may not be readily detectable using a particular oligonucleotide probe of the polynucleotide encoding GRIR, and improper or unexpected hybridization to alleles, with a locus other than the normal chromosomal locus for the polynucleotide sequence encoding GRIR. The encoded protein may also be "altered," and may contain deletions, insertions, or substitutions of amino acid residues which produce a silent change and result in a functionally equivalent GRIR. Deliberate amino acid substitutions may be made on the basis of similarity in polarity, charge, solubility, hydrophobicity, hydrophilicity, and/or the amphipathic nature of the residues, as long as the biological or immunological activity of GRIR is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of GRIR which are preferably about 5 to about 15 amino acids in length and which retain some biological activity or immunological activity of GRIR. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, pp.1–5, Cold Spring Harbor Press, Plainview, N.Y.)

The term "antagonist," as it is used herein, refers to a molecule which, when bound to GRIR, decreases the amount or the duration of the effect of the biological or immunological activity of GRIR. Antagonists may include proteins, nucleic acids, carbohydrates, antibodies, or any other molecules which decrease the effect of GRIR.

As used herein, the term "antibody" refers to intact molecules as well as to fragments thereof, such as Fab, F(ab')$_2$, and Fv fragments, which are capable of binding the epitopic determinant. Antibodies that bind GRIR polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic GRIR, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding GRIR or fragments of GRIR may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding GRIR, by northern analysis is indicative of the presence of nucleic acids encoding GRIR in a sample, and thereby correlates with expression of the transcript from the polynucleotide encoding GRIR.

A "deletion," as the term is used herein, refers to a change in the amino acid or nucleotide sequence that results in the absence of one or more amino acid residues or nucleotides.

The term "derivative," as used herein, refers to the chemical modification of GRIR, of a polynucleotide sequence encoding GRIR, or of a polynucleotide sequence complementary to a polynucleotide sequence encoding GRIR. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (Harrington, J. J. et al. (1997) Nat. Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, polymers, or any other appropriate substrate to which cells or their nucleic acids have been fixed).

"Inflammation" as used herein is interchangeable with "immune response", both terms refer to a condition associated with trauma, immune disorders, and infectious or genetic diseases and are characterized by production of cytokines, chemokines, and other signaling molecules which activate cellular and systemic defense systems.

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of GRIR. For example, modulation may cause an increase or a decrease in protein activity, binding characteristics, or any other biological, functional, or immunological properties of GRIR.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.)

The term "sample," as used herein, is used in its broadest sense. A biological sample suspected of containing nucleic acids encoding GRIR, or fragments thereof, or GRIR itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of GRIR, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of new human G-protein coupled receptors associated with immune response (GRIR), the polynucleotides encoding GRIR, and the use of these compositions for the diagnosis, treatment, or prevention of diseases associated with cell proliferation and cell signaling.

Nucleic acids encoding the GRIR-1 of the present invention were first identified in Incyte Clone 364702 from the prostate cDNA library (PROSNOT01) using a computer search for amino acid sequence alignments. A consensus sequence, SEQ ID NO:2, was derived from Incyte Clones 605666 (BRSTTUT01) and 364702 (PROSNOT01).

Figure 2A:
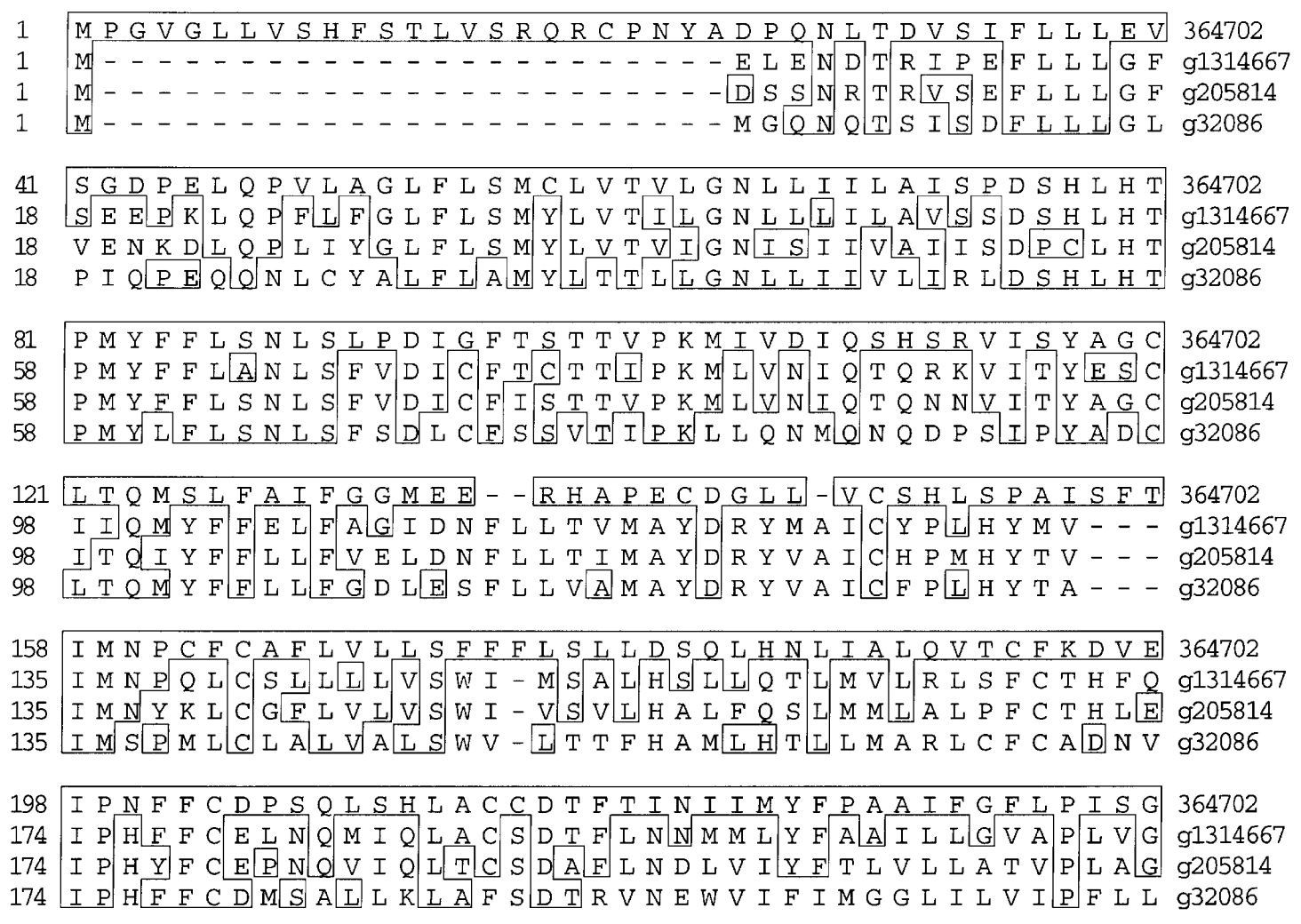

In one embodiment, the invention encompasses a polypeptide comprising the amino acid sequence of SEQ ID NO:1 as shown in FIGS. 1A, 1B, 1C, 1D and 1E. GRIR-1 is 326 amino acids in length and has two potential N glycosylation sites at $N_{28}$ and $N_{88}$, and five potential phosphorylation sites at $S_{90}$, $S_{177}$, $T_{243}$, $S_{285}$, and $S_{309}$. As shown in FIGS. 2A and 2B, GRIR-1 has chemical and structural homology with canine, rat and human olfactory receptors (g1314667, SEQ ID NO:3; g205814, SEQ ID NO:4; and g32086, SEQ ID NO:5, respectively). In particular, GRIR-1 shares 45% identity with the canine OR, 44%, with the rat OR, and 42%, with the human OR. In addition, the hydrophobic transmembrane domains are fairly well conserved among these molecules. TM1 extends from about $V_{49}$ to about $S_{73}$; TM2, from about $P_{81}$ to about $P_{102}$; TM3, from about $M_{124}$ to about $C_{141}$; TM4, from about $F_{163}$ to about $L_{182}$; Tm5, from about $I_{122}$ to about $V_{243}$; TM6, from about $P_{261}$ to about $L_{277}$; and TM7, from about $A_{289}$ to about $L_{309}$. The cysteines at $C_{120}$, $C_{147}$, $C_{164}$, and $C_{203}$ are conserved across all four receptors. The extracellular ligand binding domain from about nucleotide 712 to about nucleotide 783 is the most useful fragment of SEQ ID NO:2. Northern analysis (FIG. 5A) shows the expression of this sequence in gastrointestinal, male reproductive, and muscle cDNA libraries. Approximately 48% of these libraries are associated with neoplastic disorders and 38% with immune response.

Nucleic acids encoding the GRIR-2 of the present invention were first identified in Incyte Clone 1650519 from the prostate cDNA library (PROSTUT09) using a computer search for amino acid sequence alignments. A consensus sequence, SEQ ID NO:4, was derived from Incyte Clones 1649584, 1650519, and 1650566 (PROSTUT09); 1721996 (BLADNOT06), and 2731380 (OVARTUT04).

Figure 4B:
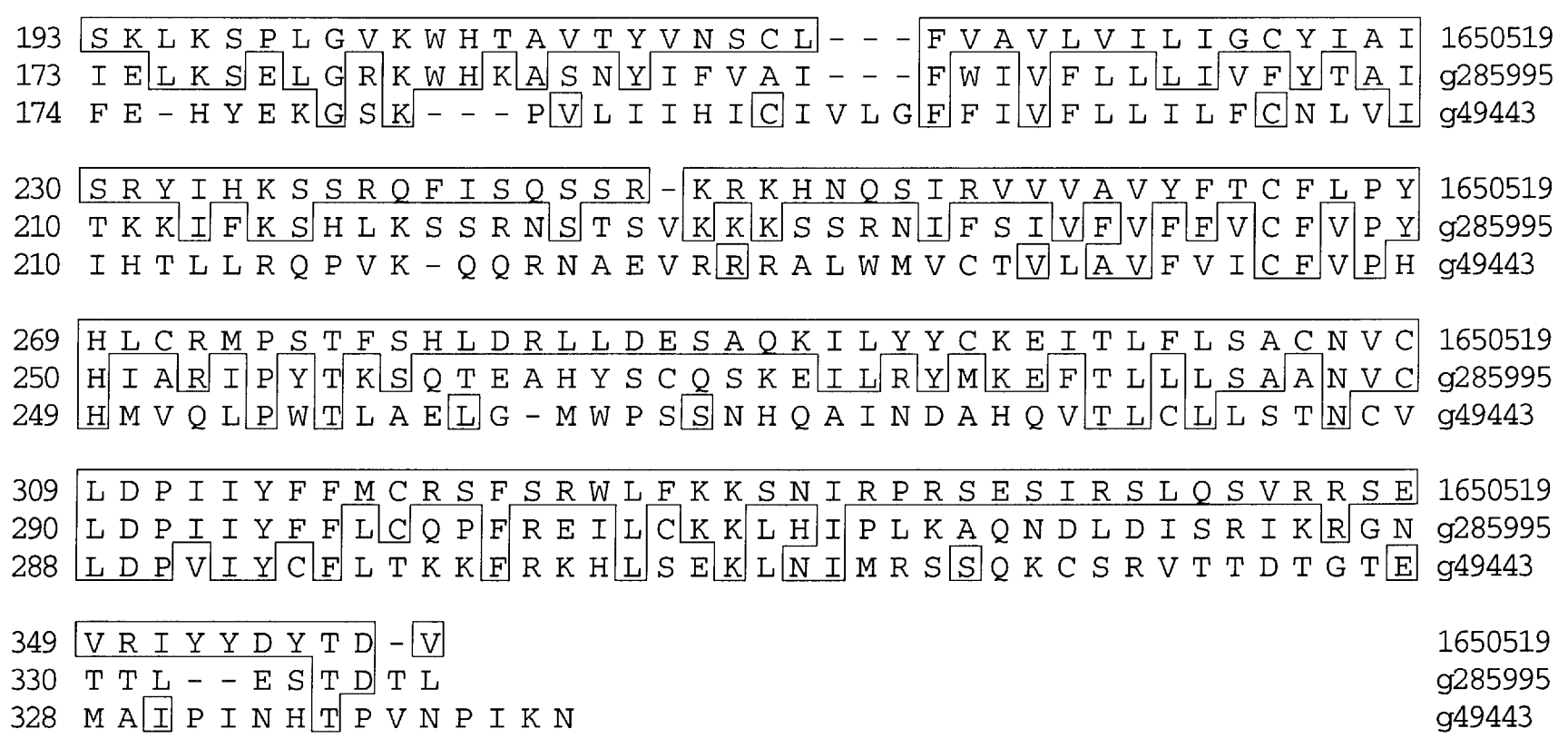

In one embodiment, the invention encompasses a polypeptide comprising the amino acid sequence of SEQ ID NO:3 as shown in FIGS. 3A, 3B, 3C, and 3D. GRIR-2 is 358 amino acids in length and has five potential N glycosylation sites at $N_4$, $N_{25}$, $N_{33}$, $N_{72}$ and $N_{251}$; and nine potential phosphorylation sites at $Y_{153}$, $S_{236}$, $S_{244}$, $S_{245}$, $S_{253}$, $S_{278}$, $S_{337}$, $S_{343}$ and $Y_{352}$. As shown in FIGS. 4A and 4B, GRIR-2 has chemical and structural homology to human KIAA0001 (g285995, SEQ ID NO:8); and rat VTR 15–20 (g49443, SEQ ID NO:9) GPCRs. Specifically, GRIR-2 shares 42% identity with KIAA0001 and 24% identity with the rat VTR15–20. In addition, the hydrophobic transmembrane domains are conserved among these molecules. TM1 extends from about $V_{44}$ to about $W_{65}$; TM2, from about $F_{78}$ to about $V_{99}$; TM3, from about $T_{127}$ to about $V_{143}$; TM4, from about $T_{158}$ to about $L_{174}$; Tm5, from about $V_{207}$ to about $C_{225}$; TM6, from about $I_{254}$ to about $S_{275}$; and TM7, from about $E_{297}$ to about $C_{318}$. The cysteine at $C_{114}$ is conserved across all three receptors. The most useful fragment of SEQ ID NO:4 encompasses the unique, extracellular ligand binding domain from about nucleotide 319 to about nucleotide 444. Northern analysis (FIG. 5B) shows the expression of this sequence in reproductive cDNA libraries. Approximately 83% of these libraries were associated with neoplastic disorders.

The invention also encompasses GRIR variants. A preferred GRIR variant is one which has at least about 80%, more preferably at least about 90%, and most preferably at least about 95% amino acid sequence identity to the GRIR amino acid sequence, and which contains at least one functional or structural characteristic of GRIR.

The invention also encompasses polynucleotides which encode GRIR-1 and GRIR-2. In a particular embodiment, the invention encompasses the polynucleotide sequences comprising the sequence of SEQ ID NO:2 and SEQ ID NO:4, which encode GRIRs.

The invention also encompasses a variant of a polynucleotide sequence encoding GRIR. In particular, such a variant polynucleotide sequence will have at least about 80%, more preferably at least about 90%, and most preferably at least about 95% polynucleotide sequence identity to the polynucleotide sequence encoding GRIR. A particular aspect of the invention encompasses a variant of SEQ ID NO:2 which has at least about 80%, more preferably at least about 90%, and most preferably at least about 95% polynucleotide sequence identity to SEQ ID NO:2. A particular aspect of the invention encompasses a variant of SEQ ID NO:4 which has at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of GRIR.

It will be appreciated by those skilled in the art that as a result of the degeneracy of the genetic code, a multitude of polynucleotide sequences encoding GRIR, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring GRIR, and all such variations are to be considered as being specifically disclosed.

Although nucleotide sequences which encode GRIR and its variants are preferably capable of hybridizing to the nucleotide sequence of the naturally occurring GRIR under appropriately selected conditions of stringency, it may be advantageous to produce nucleotide sequences encoding GRIR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GRIR and its derivatives without altering the encoded amino acid sequences include the production of RNA transcripts having more desirable properties, such as a greater half-life, than transcripts produced from the naturally occurring sequence.

The invention also encompasses production of DNA sequences which encode GRIR and GRIR derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding GRIR or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, and SEQ ID NO:4, or a fragment of SEQ ID NO:4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by GIBCO/BRL (Gaithersburg, Md.). Preferably, the process is automated with machines such as the MICRO LAB (Hamilton, Reno, Nev.), Peltier thermal cycler (PTC200; MJ Research, Watertown, Mass.) and the ABI CATALYST and 373 and 377 DNA sequencers (Perkin Elmer).

The nucleic acid sequences encoding GRIR may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode GRIR may be used in recombinant DNA molecules to direct expression of GRIR, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express GRIR.

As will be understood by those of skill in the art, it may be advantageous to produce ABBR-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter GRIR encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding GRIR may be ligated to a heterologous sequence to encode a fusion protein. For example, to screen peptide libraries for inhibitors of GRIR activity, it may be useful to encode a chimeric GRIR protein that can be recognized by a commercially available antibody. A fusion protein may also be engineered to contain a cleavage site located between the GRIR encoding sequence and the heterologous protein sequence, so that GRIR may be cleaved and purified away from the heterologous moiety.

In another embodiment, sequences encoding GRIR may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 225–232.) Alternatively, the protein itself may be produced using chemical methods to synthesize the amino acid sequence of GRIR, or a fragment thereof. For example, peptide synthesis can be performed using various solid-phase techniques (Roberge, J. Y. et al. (1995) Science 269:202–204) and automated synthesis may be achieved using the ABI 431A peptide synthesizer (Perkin Elmer).

The newly synthesized peptide may be substantially purified by preparative high performance liquid chromatography. (Chiez, R. M. and Regnier, F. Z. (1990) Methods Enzymol. 182:392–421.) The composition of the synthetic peptides may be confirmed by amino acid analysis or by sequencing. (the Edman degradation procedure described in Creighton, T. (1983) *Proteins, Structures and Molecular Properties*, WH Freeman and Co., New York, N.Y.) Additionally, the amino acid sequence of GRIR, or any part thereof, may be altered during direct synthesis and/or combined with sequences from other proteins, or any part thereof, to produce a variant polypeptide.

In order to express a biologically active GRIR, the nucleotide sequences encoding GRIR or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding GRIR and appropriate transcriptional and translational control elements. These methods include in vitro recombinant DNA techniques, synthetic techniques, and in vivo genetic recombination. Such techniques are described in Sambrook, J. et al. (1989; *Molecular Cloning, A Laboratory Manual*, ch. 4, 8, and 16–17, Cold Spring Harbor Press, Plainview, N.Y.) and Ausubel, F. M. et al. (1995 and periodic supplements; *Current Protocols in Molecular Biology*, ch. 9, 13, and 16, John Wiley & Sons, New York, N.Y.).

A variety of expression vector/host systems may be utilized to contain and express sequences encoding GRIR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus);

plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding GRIR, vectors based on SV40 or EBV may be used with an appropriate selectable marker.

In bacterial systems, a number of expression vectors may be selected depending upon the use intended for GRIR. For example, when large quantities of GRIR are needed for the induction of antibodies, vectors which direct high level expression of fusion proteins that are readily purified may be used. Such vectors include, but are not limited to, multifunctional $E.$ $coli$ cloning and expression vectors such as BLUESCRIPT (Stratagene), in which the sequence encoding GRIR may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503–5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast $Saccharomyces$ $cerevisiae$, a number of vectors containing constitutive or inducible promoters, such as alpha factor, alcohol oxidase, and PGH, may be used. For reviews, see Ausubel (supra) and Grant et al. (1987; Methods Enzymol. 153:516–544).

In cases where plant expression vectors are used, the expression of sequences encoding GRIR may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, for example, Hobbs, S. or Murry, L. E. in $McGraw$ $Hill$ $Yearbook$ $of$ $Science$ $and$ $Technology$ (1992) McGraw Hill, New York, N.Y.; pp. 191–196.)

An insect system may also be used to express GRIR. For example, in one such system, $Autographa$ $californica$ nuclear polyhedrosis virus (AcNPV) is used as a vector to express foreign genes in $Spodoptera$ $frugiperda$ cells or in $Trichoplusia$ $larvae$. The sequences encoding GRIR may be cloned into a non-essential region of the virus, such as the polyhedrin gene, and placed under control of the polyhedrin promoter. Successful insertion of GRIR will render the polyhedrin gene inactive and produce recombinant virus lacking coat protein. The recombinant viruses may then be used to infect, for example, $S.$ $frugiperda$ cells or Trichoplusia larvae in which GRIR may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding GRIR may be ligated into an adenovirus transcription/translation complex consisting of the late promoter and tripartite leader sequence. Insertion in a non-essential E1 or E3 region of the viral genome may be used to obtain a viable virus which is capable of expressing GRIR in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding GRIR. Such signals include the ATG initiation codon and adjacent sequences. In cases where sequences encoding GRIR and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing GRIR can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyltransferase genes (Lowy, I. et al. (1980) Cell 22:817–23), which can be employed in tk⁻ or apr⁻ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al (1981) J. Mol. Biol. 150:1–14); and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding GRIR is inserted within a marker gene sequence, transformed cells containing sequences encoding GRIR can be identified by the absence of marker gene function. Alternatively, a marker gene can be placed in tandem with a sequence encoding GRIR under the control of a single promoter. Expression of the marker gene in response to induction or selection usually indicates expression of the tandem gene as well.

Alternatively, host cells which contain the nucleic acid sequence encoding GRIR and express GRIR may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein sequences.

The presence of polynucleotide sequences encoding GRIR can be detected by DNA—DNA or DNA-RNA hybridization or amplification using probes or fragments or fragments of polynucleotides encoding GRIR. Nucleic acid amplification based assays involve the use of oligonucleotides or oligomers based on the sequences encoding GRIR to detect transformants containing DNA or RNA encoding GRIR.

A variety of protocols for detecting and measuring the expression of GRIR, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on GRIR is preferred, but a competitive binding assay may be employed. These and other assays are well described in the art, for example, in Hampton, R. et al. (1990; Serological Methods, a Laboratory Manual, Section IV, APS Press, St Paul, Minn.) and in Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GRIR include oligolabeling, nick translation, end-labeling, or PCR amplification using a labeled nucleotide. Alternatively, the sequences encoding GRIR, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding GRIR may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode GRIR may be designed to contain signal sequences which direct secretion of GRIR through a prokaryotic or eukaryotic cell membrane. Other constructions may be used to join sequences encoding GRIR to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the GRIR encoding sequence may be used to facilitate purification. One such expression vector provides for expression of a fusion protein containing GRIR and a nucleic acid encoding 6 histidine residues preceding a thioredoxin or an enterokinase cleavage site. The histidine residues facilitate purification on immobilized metal ion affinity chromatography (IMIAC; described in Porath, J. et al. (1992) Prot. Exp. Purif. 3: 263–281), while the enterokinase cleavage site provides a means for purifying GRIR from the fusion protein. A discussion of vectors which contain fusion proteins is provided in Kroll, D. J. et al. (1993; DNA Cell Biol. 12:441–453).

Fragments of GRIR may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, for example, using the Applied Biosystems 431A peptide synthesizer (Perkin Elmer). Various fragments of GRIR may be synthesized separately and then combined to produce the full length molecule.

THERAPEUTICS

Chemical and structural homology exists among GRIR-1, and canine, rat and human olfactory receptors (g1314667, SEQ ID NO:5; g205814, SEQ ID NO:6; and g32086, SEQ ID NO:7, respectively). In addition, GRIR-1 is expressed in gastrointestinal, male reproductive, and muscle cDNA libraries. Approximately 48% of these libraries are associated with neoplastic disorders and 38%, with immune response. Therefore, GRIR-1 appears to play a role in cell proliferation and cell signaling.

Chemical and structural homology exists among GRIR-2, human KIAA0001 (g285995, SEQ ID NO:8); and rat VTR 15–20 (g49443, SEQ ID NO:9) GPCRs. In addition, GRIR-2 is expressed primarily reproductive tissues. Approximately 80% of these libraries are associated with neoplastic disorders. Therefore, GRIR-2 appears to play a role in cell proliferation and cell signaling.

In one embodiment, an antagonist of GRIR may be administered to a subject to treat or prevent a neoplastic disorder. Neoplastic disorders may include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector expressing the complement of the polynucleotide encoding GRIR may be administered to a subject to treat or prevent a neoplastic disorder including, but not limited to, those described above.

In an additional embodiment, an antagonist of GRIR may be administered to a subject to treat or prevent an immune response. Immune responses may be associated with, but are not limited to: AIDS, Addison's disease, adult respiratory distress syndrome, allergies, anaphylaxis, ankylosing spondylitis, amyloidosis, anemia, asthma, atherosclerosis, autoimmune hemolytic anemia, autoimmune thyroiditis bronchitis, bursitis, cholecystitis, cirrhosis, contact dermatitis, Crohn's disease, cystic fibrosis, atopic dermatitis, dermatomyositis, diabetes mellitus, emphysema, erythema nodosum, atrophic gastritis, glomerulonephritis, Goodpasture's syndrome, gout, Graves' disease, chronic granulomatous disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, psoriasis, rheumatoid arthritis, scleroderma, sickle cell anemia, Sjögren's syndrome, systemic sclerosis, thalassemia, ulcerative colitis, Werner syndrome, and complications of cancer, hemodialysis, and extracorporeal circulation; viral, bacterial, fungal, parasitic, protozoal, and helminthic infections; and trauma.

In another embodiment, a vector expressing the complement of the polynucleotide encoding GRIR may be administered to a subject to treat or prevent an immune response including, but not limited to, those described above.

In one aspect, an antibody which specifically binds GRIR may be used directly as an antagonist or indirectly as a targeting or delivery mechanism for bringing a pharmaceutical agent to cells or tissues which express GRIR.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of GRIR may be produced using methods which are generally known in the art. In particular, purified GRIR may be used to produce antibodies or to screen libraries of pharmaceutical agents to identify those which specifically bind GRIR. Antibodies to GRIR may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with GRIR or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to GRIR have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of GRIR amino acids may be fused with those of another protein, such as KLH, and antibodies to the chimeric molecule may be produced.

Monoclonal antibodies to GRIR may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce ABBR-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1 991) Nature 349:293–299.)

Antibody fragments which contain specific binding sites for GRIR may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GRIR and its specific antibody. A two-site, monoclonal-based immunoassay utilizing monoclonal antibodies reactive to two non-interfering GRIR epitopes is preferred, but a competitive binding assay may also be employed. (Maddox, supra.)

In another embodiment of the invention, the polynucleotides encoding GRIR, or any fragment or complement thereof, may be used for therapeutic purposes. In one aspect, the complement of the polynucleotide encoding GRIR may be used in situations in which it would be desirable to block the transcription of the mRNA. In particular, cells may be transformed with sequences complementary to polynucleotides encoding GRIR. Thus, complementary molecules or fragments may be used to modulate GRIR activity, or to achieve regulation of gene function. Such technology is now well known in the art, and sense or antisense oligonucleotides or larger fragments can be designed from various locations along the coding or control regions of sequences encoding GRIR.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding GRIR. These techniques are described, for example, in Sambrook (supra) and in Ausubel (supra).

Genes encoding GRIR can be turned off by transforming a cell or tissue with expression vectors which express high levels of a polynucleotide or fragment thereof encoding GRIR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding GRIR. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, *Molecular and Immunologic Approaches*, pp. 163–177, Futura Publishing Co., Mt. Kisco, N.Y.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding GRIR.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GRIR. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of GRIR, antibodies to GRIR, and mimetics, agonists, antagonists, or inhibitors of GRIR. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of GRIR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example GRIR or fragments thereof, antibodies of GRIR, and agonists, antagonists or inhibitors of GRIR, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind GRIR may be used for the diagnosis of disorders characterized by expression of GRIR, or in assays to monitor patients being treated with GRIR or agonists, antagonists, and inhibitors of GRIR. Antibodies useful for diagnostic purposes may be prepared in the same manner as those described above for therapeutics. Diagnostic assays for GRIR include methods which utilize the antibody and a label to detect GRIR in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring GRIR, including ELISAs, RIAs, and FACS, are known in the art and provide a basis for diagnosing altered or abnormal levels of GRIR expression. Normal or standard values for GRIR expression are established by combining body fluids or cell extracts taken from normal mammalian subjects, preferably human, with antibody to GRIR under conditions suitable for complex formation The amount of standard complex formation may be quantified by various methods, preferably by photometric means. Quantities of GRIR expressed in subject samples from biopsied tissues are compared with the standard values. Deviation between standard and subject values establishes the parameters for diagnosing disease.

In another embodiment of the invention, the polynucleotides encoding GRIR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of GRIR may be correlated with disease. The diagnostic assay may be used to distinguish between absence, presence, and excess expression of GRIR, and to monitor regulation of GRIR levels during therapeutic intervention.

In one aspect, hybridization with PCR probes which are capable of detecting polynucleotide sequences, including genomic sequences, encoding GRIR or closely related molecules may be used to identify nucleic acid sequences which encode GRIR. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding GRIR, alleles, or related sequences.

Probes may also be used for the detection of related sequences, and should preferably contain at least 50% of the nucleotides from any of the GRIR encoding sequences. The hybridization probes of the subject invention may be DNA or RNA and may be derived from the sequences of SEQ ID NO:2, SEQ ID NO:4, or from genomic sequences including promoter and enhancer elements and introns of the naturally occurring GRIR.

Means for producing specific hybridization probes for DNAs encoding GRIR include the cloning of polynucleotide sequences encoding GRIR or GRIR derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding GRIR may be used for the diagnosis of a disorder associated with expression of GRIR. Examples of a neoplastic disorder include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. Examples of an immune response may be associated with, but are not limited to: AIDS, Addison's disease, adult respiratory distress syndrome, allergies, anaphylaxis, ankylosing spondylitis, amyloidosis, anemia, asthma, atherosclerosis, autoimmune hemolytic anemia, autoimmune thyroiditis, bronchitis, bursitis, cholecystitis, cirrhosis, contact dermatitis, Crohn's disease, cystic fibrosis, atopic dermatitis, dermatomyositis, diabetes mellitus, emphysema, erythema nodosum, atrophic gastritis, glomerulonephritis, Goodpasture's syndrome, gout, Graves' disease, chronic granulomatous disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, psoriasis, rheumatoid arthritis, scleroderma, sickle cell anemia, Sjögren's syndrome, systemic sclerosis, thalassemia, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding GRIR may be used in Southern or northern analysis, dot blot, or other membrane-based technologies; in PCR technologies; in dipstick, pin, and ELISA assays; and in microarrays utilizing fluids or tissues from patient biopsies to detect altered GRIR expression. Such qualitative or quantitative methods are well known in the art.

In a particular aspect, the nucleotide sequences encoding GRIR may be useful in assays that detect the presence of associated disorders, particularly those mentioned above. The nucleotide sequences encoding GRIR may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding GRIR in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of GRIR, a normal or standard profile for expression is established. This may be accomplished by combining body fluids or cell extracts taken from normal subjects, either animal or human, with a sequence, or a fragment thereof, encoding GRIR, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GRIR may involve the use of PCR. These oligomers may be chemically synthesized, generated enzymatically, or produced in vitro. Oligomers will preferably contain a fragment of a polynucleotide encoding GRIR, or a fragment of a polynucleotide complementary to the polynucleotide encoding GRIR, and will be employed under optimized conditions for identification of a specific gene or condition. Oligomers may also be employed under less stringent conditions for detection or quantitation of closely related DNA or RNA sequences.

Methods which may also be used to quantitate the expression of GRIR include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1996; Nat. Biotech. 14:1675–1680), and Schena, M. et al. (1996; Proc. Natl. Acad. Sci. 93:10614–10619).

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251116 (Baldeschweiler et al.). In another aspect, a grid array analogous to a dot or slot blot (HYBRIDOT® apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including Brinkmann® multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.)

In another embodiment of the invention, nucleic acid sequences encoding GRIR may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions, or single chromosome cDNA libraries, such as those reviewed in Price, C. M. (1993; Blood Rev. 7:127–134) and Trask, B. J. (1991; Trends Genet. 7:149–154).

Fluorescent in situ hybridization (FISH, as described, e.g., in Heinz-Ulrich, et al. (1995) in Meyers, R. A. (ed.) *Molecular Biology and Biotechnology*, pp. 965–968, VCH Publishers New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding GRIR on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, GRIR, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between GRIR and the agent being tested may be measured.

Another technique for drug screening which may be used provides for high throughput screening of compounds having suitable binding affinity to the protein of interest as described in published PCT application WO84/03564 (Geysen, et al.). In this method, large numbers of different small test compounds are synthesized on a solid substrate, such as plastic pins or some other surface. The test compounds are reacted with GRIR, or fragments thereof, and washed. Bound GRIR is then detected by methods well known in the art. Purified GRIR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GRIR specifically compete with a test compound for binding GRIR. In this manner, antibodies can be used to detect the presence of any peptide which shares one or more antigenic determinants with GRIR.

In additional embodiments, the nucleotide sequences which encode GRIR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. PROSNOT01 Cloning and Isolation of cDNAs

The prostate tissue used for library construction was obtained from a 78 year-old Caucasian male with leukemia (Lot No. 94-039, International Institute for the Advancement of Medicine, Exton Pa.). Patient history included skin cancer, emphysema, asthma, and a surgery for cholecystectomy. The patient was taking hydroxyurea for his leukemia.

The prostate tissue was flash frozen, ground in a mortar and pestle, lysed immediately in buffer containing guanidinium isothiocyanate and spun through cesium chloride. The lysate was extracted twice with phenol chloroform at pH 8.0 and centrifuged over a CsCl cushion using an Beckman SW28 rotor in a Beckman L8-70M ultracentrifuge (Beckman Instruments). The RNA was precipitated using 0.3 M sodium acetate and 2.5 volumes of ethanol, resuspended in water and treated with DNase for 15 min at 37° C. The RNA was isolated using the Qiagen Oligotex kit (QIAGEN Inc., Chatsworth Calif.) and used to construct the cDNA library.

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was digested with XhoI restriction enzyme and fractionated on Sephacryl S400 to obtain sequences which exceeded 1000 bp in size. The size selected cDNAs were inserted into the LambdaZap® vector system (Stratagene, La Jolla Calif.); and the vector, which contains the pBluescript™ phagemid (Stratagene), was transformed into E. coli, strain XL1-BlueMRF™ (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

Plasmid DNA was released from the cells and purified using the R.E.A.L. PREP 96 Plasmid Kit for Rapid Extraction Alkaline Lysis Plasmid Minipreps (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

Phagemid DNA was released from the cells and purified using the Miniprep Kit (Catalog #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, GIBCO/BRL) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA purification system (Catalog #A7100, Promega, Madison Wis.) or QIAwell™-8 Plasmid, QIAwell PLUS DNA and QIAwell ULTRA DNA purification systems (QIAGEN).

II. PROSTUT09 Cloning and Isolation of cDNAs

For the PROSTUT09 cDNA library, prostate tumor was obtained from a 66-year-old Caucasian male. Surgery included a radical prostatectomy, a radical cystectomy, and a urinary diversion to the intestine. The pathology report indicated an invasive grade 3 (of 3) transitional cell carcinoma located within the prostatic urethra which extended to involve periprostatic glands and diffusely invade the prostatic parenchyma anteriorly and posteriorly. All final surgical margins including ureters (left and right, after multiple re-excisions) and prostatic urethra were negative for tumor. In addition to extensive involvement by transitional cell carcinoma, the right prostate contained a microscopic focus of adenocarcinoma, Gleason grade 3+2, which was confined to the prostate and showed no capsular penetration. Multiple right and left pelvic lymph nodes were negative for tumor. The patient presented with prostatic inflammatory disease. The patient history included a previous transurethral prostatectomy, neoplasm of the lung, benign hypertension, and tobacco use. The patient was taking insulin and Dyazide® (diuretic/antihypertensive; SmithKline Beecham Pharmaceuticals, Philadelphia, Pa.) at the time of surgery.

The frozen tissue was homogenized and lysed using a Brinkmann Homogenizer Polytron PT-3000 (Brinkmann Instruments, Westbury, N.J.) in guanidinium isothiocyanate solution. The lysates were centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. RNA extraction and precipitation were repeated as before. The mRNA was isolated using the Qiagen Oligotex kit (QIAGEN) and used to construct the cDNA libraries.

The mRNA was handled according to the recommended protocols in the SuperScript Plasmid System for cDNA synthesis and plasmid cloning (Catalog #18248-013, Gibco/BRL).The cDNAs were fractionated on a Sepharose CL4B column (Catalog #275105-01; Pharmacia), and those cDNAs exceeding 400 bp were ligated into pINCY 1. The plasmid pINCY 1 was subsequently transformed into DH5a™ competent cells (Catalog #18258-012; Gibco/BRL)

III. Sequencing and Homology Searching of cDNA Clones and Deduced Proteins

The cDNAs for PROSNOT01 and PROSTUT09 were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer). Reading frame was determined.

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992; Protein Engineering 5:35–51), could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (Sambrook, supra, ch. 7 and Ausubel, F. M. et al. supra, ch. 4 and 16.)

Analogous computer techniques applying BLAST are used to search for identical or related molecules in nucleotide databases such as GenBank or the LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

% sequence identity×% maximum BLAST score/100

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding GRIR occurs. Abundance and percent abundance are also reported. Abundance directly reflects the number of times a particular transcript is represented in a cDNA library, and percent abundance is abundance divided by the total number of sequences examined in the cDNA library.

V. Extension of GRIR Encoding Polynucleotides

The nucleic acid sequences of Incyte Clones 364702 and 1650519 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer—primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

Step 1 94° C. for 1 min (initial denaturation)

Step 2 65° C. for 1 min

Step 3 68° C. for 6 min

Step 4 94° C. for 15 sec

Step 5 65° C. for 1 min

Step 6 68° C. for 7 min

Step 7 Repeat steps 4 through 6 for an additional 15 cycles

Step 8 94° C. for 15 sec

Step 9 65° C. for 1 min

Step 10 68° C. for 7:15 min

Step 11 Repeat steps 8 through 10 for an additional 12 cycles

Step 12 72° C. for 8 min

Step 13 4° C. (and holding)

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (Sambrook, supra, Appendix A, p. 2.) After incubation for one hour at 37° C., the E. coli mixture was plated on Luria Bertani (LB) agar (Sambrook, supra, Appendix A, p. 1) containing 2× Carb. The following day, several colonies were randomly picked from each plate and cultured in 150 µl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well. Amplification was performed using the following conditions:

Step 1 94° C. for 60 sec

Step 2 94° C. for 20 sec

Step 3 55° C. for 30 sec

Step 4 72° C. for 90 sec

Step 5 Repeat steps 2 through 4 for an additional 29 cycles

Step 6 72° C. for 180 sec

Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 or SEQ ID NO:4 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer and 250 μCi of [$\gamma$-$^{32}$P] adenosine triphosphate (Amersham) and T4 polynucleotide kinase (DuPont NEN®, Boston, Mass.). The labeled oligonucleotides are substantially purified using a Sephadex G-25 superfine resin column (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process, such as that described in Chee (supra.)

In the alternative, a chemical coupling procedure and an ink jet device are used to synthesize oligomers on the surface of a substrate. (Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/expression level of each oligonucleotide sequence in the microarray.

VIII. Complementary Polynucleotides

Sequences complementary to the GRIR-encoding sequences, or any parts thereof, are used to detect, decrease, or inhibit expression of naturally occurring GRIR. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of GRIR. To inhibit transcription, a complementary oligonucleotide is designed from the most unique 5' sequence and used to prevent promoter binding to the coding sequence. To inhibit translation, a complementary oligonucleotide is designed to prevent ribosomal binding to the GRIR-encoding transcript.

IX. Expression of GRIR

Expression of GRIR is accomplished by subcloning the cDNAs into appropriate vectors and transforming the vectors into host cells. In this case, the cloning vector is also used to express GRIR in *E. coli*. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of GRIR into bacterial growth media which can be used directly in the following assay for activity.

X. Demonstration of GRIR Activity

Receptors such as those encoded by SEQ ID NOs:2 and 4 may be expressed in heterologous expression systems and their biological activity tested utilizing the purinergic receptor system ($P_{2U}$) as published by Erb, et al. (1993; Proc. Natl. Acad. Sci. 90:10449–53.) Because cultured K562 human leukemia cells lack $P_{2U}$ receptors, they can be transfected with expression vectors containing either normal or chimeric $P_{2U}$ and loaded with fura-, fluorescent probe for $Ca^{++}$. Activation of properly assembled and functional extracellular SP-transmembrane/intracellular $P_{2U}$ receptors with extracellular UTP or ATP mobilizes intracellular $Ca^{++}$ which reacts with fura- and is measured spectrofluorometrically. Bathing the transfected K562 cells in microwells containing appropriate ligands will trigger binding and fluorescent activity defining effectors of SP. Once ligand and function are established, the $P_{2U}$ system is useful for defining antagonists or inhibitors which block binding and prevent such fluorescent reactions.

XI. Production of GRIR Specific Antibodies

GRIR substantially purified using PAGE electrophoresis (Harrington, M. G. (1990) Methods Enzymol. 182:488–495), or other purification techniques, is used to immunize rabbits and to produce antibodies using standard protocols. The GRIR amino acid sequence is analyzed using DNASTAR software (DNASTAR Inc) to determine regions of high immunogenicity, and a corresponding oligopeptide is synthesized and used to raise antibodies by means known to those of skill in the art. Selection of appropriate epitopes, such as those near the C-terminus or in hydrophilic regions, is described by Ausubel F. M. et al. (1995 and periodic supplements) Current Protocols in Molecular Biology, ch. 11, John Wiley & Sons, New York, N.Y. and by others.

Typically, the oligopeptides are 15 residues in length, and are synthesized using an Applied Biosystems Peptide Synthesizer Model 431 A using fmoc-chemistry and coupled to KLH (Sigma, St. Louis, Mo.) by reaction with N-maleimidobenzoyl-N-hydroxysuccinimide ester (MBS), following the procedure described in Ausubel et al., supra. Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring GRIR Using Specific Antibodies

Naturally occurring or recombinant GRIR is substantially purified by immunoaffinity chromatography using antibodies specific for GRIR. An immunoaffinity column is constructed by covalently coupling GRIR antibody to an activated chromatographic resin, such as CNBr-activated Sepharose (Pharmacia & Upjohn). After the coupling, the resin is blocked and washed according to the manufacturer's instructions.

Media containing GRIR are passed over the immunoaffinity column, and the column is washed under conditions that allow the preferential absorbance of GRIR (e.g., high ionic strength buffers in the presence of detergent). The column is eluted under conditions that disrupt antibody/ABBR binding (e.g., a buffer of pH 2 to pH 3, or a high concentration of a chaotrope, such as urea or thiocyanate ion), and GRIR is collected.

XIII. Identification of Molecules Which Interact with GRIR

GRIR or biologically active fragments thereof are labeled with $^{125}I$ Bolton-Hunter reagent. (Bolton et al. (1973) Biochem. J. 133:529.) Candidate molecules previously arrayed in the wells of a multi-well plate are incubated with the labeled GRIR, washed, and any wells with labeled GRIR complex are assayed. Data obtained using different concentrations of GRIR are used to calculate values for the number, affinity, and association of GRIR with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide comprising an amino acid sequence selected from the group consisting of SEQ ID NO:1 and SEQ ID NO:3.

2. An isolated and purified composition comprising the polynucleotide of claim 1 and a pharmaceutically acceptable carrier.

3. An expression vector comprising the polynucleotide of claim 1.

4. A host cell comprising the expression vector of claim 3.

5. A method for producing a polypeptide comprising the amino acid sequence selected from the group consisting of SEQ ID NO:1 and SEQ ID NO:3, the method comprising the steps of:

(a) culturing the host cell of claim 4 under conditions suitable for the expression of the polypeptide; and (b) recovering the polypeptide from the host cell culture.

6. An isolated and purified polynucleotide which hybridizes under stringent conditions of 50% formamide 5× SSPE, 0.3% SDS, and 200 µg/ml sheared and denatured salmon sperm DNA at 42° C. to a polynucleotide encoding a polypeptide comprising an amino acid sequence selected from the group consisting of SEQ ID NO:1 and SEQ ID NO:3.

7. An isolated and purified polynucleotide which is completely complementary to a polynucleotide encoding a polypeptide comprising an amino acid sequence selected from the group consisting of SEQ ID NO:1 and SEQ ID NO:3.

8. A method for detecting a polynucleotide encoding a polypeptide comprising an amino acid sequence selected from the group consisting of SEQ ID NO:1 or SEQ ID NO:3 in a biological sample containing nucleic acids, the method comprising the steps of:

(a) hybridizing the polynucleotide of claim 7 to at least one of the nucleic acids in the biological sample, thereby forming a hybridization complex; and (b) detecting the hybridization complex, wherein the presence of the hybridization complex correlates with the presence of the polynucleotide encoding the polypeptide in the biological sample.

9. The method of claim 8 wherein the nucleic acids of the biological sample are amplified by the polymerase chain reaction prior to the hybridizing step.

10. An isolated and purified polynucleotide selected from the group consisting of SEQ ID NO:2 and SEQ ID NO:4.

11. A fragment of a polynucleotide selected from the group consisting of SEQ ID NO:2 and SEQ ID NO:4, wherein the fragment is selected from the group consisting of:
a) nucleotides 712 through nucleotide 783 of SEQ ID NO:2; and
b) nucleotides 319 through 444 of SEQ ID NO:4.

12. An isolated and purified polynucleotide which is completely complementary to a polynucleotide selected from the group consisting of SEQ ID NO:2 and SEQ ID NO:4.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 326 amino acids
      (B) TYPE: amino acid
      (C) STRANDEDNESS: single
      (D) TOPOLOGY: linear (vii) IMMEDIATE SOURCE:
      (A) LIBRARY: PROSNOT01
      (B) CLONE: 364702

(xi) SEQUENCE DESCRIPTION: SEQ ID NO:1:

```
Met Pro Gly Val Gly Leu Leu Val Ser His Phe Ser Thr Leu Val Ser
1               5                   10                  15

Arg Gln Arg Cys Pro Asn Tyr Ala Asp Pro Gln Asn Leu Thr Asp Val
            20                  25                  30

Ser Ile Phe Leu Leu Leu Glu Val Ser Gly Asp Pro Glu Leu Gln Pro
        35                  40                  45
```

```
Val Leu Ala Gly Leu Phe Leu Ser Met Cys Leu Val Thr Val Leu Gly
 50                  55                  60

Asn Leu Leu Ile Ile Leu Ala Ile Ser Pro Asp Ser His Leu His Thr
 65                  70                  75                  80

Pro Met Tyr Phe Phe Leu Ser Asn Leu Ser Leu Pro Asp Ile Gly Phe
                 85                  90                  95

Thr Ser Thr Thr Val Pro Lys Met Ile Val Asp Ile Gln Ser His Ser
                100                 105                 110

Arg Val Ile Ser Tyr Ala Gly Cys Leu Thr Gln Met Ser Leu Phe Ala
            115                 120                 125

Ile Phe Gly Gly Met Glu Glu Arg His Ala Pro Glu Cys Asp Gly Leu
        130                 135                 140

Leu Val Cys Ser His Leu Ser Pro Ala Ile Ser Phe Thr Ile Met Asn
145                 150                 155                 160

Pro Cys Phe Cys Ala Phe Leu Val Leu Leu Ser Phe Phe Leu Ser
                165                 170                 175

Leu Leu Asp Ser Gln Leu His Asn Leu Ile Ala Leu Gln Val Thr Cys
            180                 185                 190

Phe Lys Asp Val Glu Ile Pro Asn Phe Phe Cys Asp Pro Ser Gln Leu
        195                 200                 205

Ser His Leu Ala Cys Cys Asp Thr Phe Thr Ile Asn Ile Ile Met Tyr
    210                 215                 220

Phe Pro Ala Ala Ile Phe Gly Phe Leu Pro Ile Ser Gly Thr Phe Ser
225                 230                 235                 240

Leu Thr Val Lys Ile Leu Ser Ser Ile Leu Arg Val Ser Ser Ser Gly
                245                 250                 255

Gly Lys Tyr Lys Pro Ser Pro Val Gly Leu Thr Cys Gln Leu Phe
            260                 265                 270

Ala Gly Gly Tyr Leu Gly Ser Asp Val Ser Ser Pro Arg Lys Ser
        275                 280                 285

Ala Val Ala Ser Val Met Tyr Thr Val Val Thr Pro Met Leu Asn Pro
290                 295                 300

Phe Met Tyr Ser Leu Arg Asn Arg Asp Met Lys Ser Val Leu Arg Arg
305                 310                 315                 320

Pro His Gly Ser Thr Val
                325
```

(2) INFORMATION FOR SEQ ID NO:2:

(i) SEQUENCE CHARACTERISTICS:
        (A) LENGTH: 1828 base pairs
        (B) TYPE: nucleic acid
        (C) STRANDEDNESS: single
        (D) TOPOLOGY: linear (vii) IMMEDIATE SOURCE:
        (A) LIBRARY: PROSNOT01
        (B) CLONE: 364702

(xi) SEQUENCE DESCRIPTION: SEQ ID NO:2:

```
GGCCAGGACG GTGTCGATCT CCTAACCCCG TGATCTGCCC TCCTCAGCCT CCCAGAGTGC    60

TGGGACTACA GGCGTGAGCC ACCGCATCTG GCCAAACTTT CTGATGAAAA CTCTAAGTCC   120

ACCTAAGCTA AGGACAGGAG TTACAGCTTC CATGAATTTT AAAACCAGAC CCACCGATTT   180

GAGTAAGCAA TTACTCTCTT GAAGGAGAAA AGTCAGAAAA CATAATGATG AAATCACTAG   240

GACCTAACTG GCATGTGGAA TTATTTTCTG CTTATGAACT ATCAACTTTA ATTTCATTTC   300
```

-continued

```
CAGATGACAT GGTCTCAGCT GTTCTACAGT GTTTATAAAT GTTCTAAATC AAGGGAATTC    360

ATCAATCTAG TAGAATAAAA TATTTGAGTT CTTAATTTCC TTTAATTAGG ATAACCTTTT    420

TCTTCAAGTG AAGAGAATGG TTTTATTACA TAGTTTTCTT CGGAAAAGAT AGGCTGTATT    480

TTCTAGCAGT TACGAATTTG TTATGTATGA TGATCTGGTT CTTGGAACAT TCTTGAATCT    540

AGTGTCTCTA AGGCAGGTGT GTACAGCAAG AAGTGAATAA CACAGAAATC AATGATGAAA    600

GCATTAGAAG ACAATTGAGT CTGTCAGAAC TGCAAAATAT TGCTGAGTGT GGATTGCTCT    660

GAAATCTGAA AACATTACTT GTGAATTGCT TCTATTCAAA ATGCAGACAC AATGCCAGGT    720

GTTGGTTTAC TTGTTTCCCA TTTTTCAACC CTCGTTTCTA GGCAAAGGTG TCCAAATTAT    780

GCAGACCCAC AGAATCTAAC AGATGTCTCT ATATTCCTCC TCCTAGAAGT CTCAGGGGAT    840

CCAGAACTGC AGCCAGTCCT TGCTGGGCTG TTCCTGTCCA TGTGCCTGGT CACGGTGCTG    900

GGGAACCTGC TCATCATCCT GGCCATCAGC CCTGACTCCC ACCTCCACAC CCCCATGTAC    960

TTCTTCCTCT CCAACCTGTC CTTGCCTGAC ATCGGTTTCA CCTCCACCAC GGTCCCCAAG   1020

ATGATTGTGG ACATCCAGTC TCACAGCAGA GTCATCTCCT ATGCAGGCTG CCTGACTCAG   1080

ATGTCTCTCT TTGCCATTTT TGGAGGCATG GAAGAGAGAC ATGCTCCTGA GTGTGATGGC   1140

CTATGACTGG TTTGTAGCCA TCTGTCACCC GCTATATCAT TCACCATCAT GAACCCGTGT   1200

TTCTGTGCCT TTCTAGTTTT GTTGTCTTTT TTTTTTCTCA GTCTTTTAGA CTCCCAGCTG   1260

CACAACTTGA TTGCCTTACA AGTGACCTGC TTCAAGGATG TGGAAATTCC TAATTTCTTC   1320

TGTGACCCTT CTCAACTCTC CCATCTTGCA TGTTGTGACA CCTTCACCAT TAACATAATC   1380

ATGTATTTCC CTGCTGCCAT ATTTGGTTTT CTTCCCATCT CAGGGACCTT TTCTCTTACT   1440

GTAAAAATTC TTTCCTCCAT TCTGAGGGTT TCATCATCAG GTGGGAAGTA TAAACCTTCT   1500

CCACCTGTGG GTCTCACCTG TCAGTTGTTT GCTGGAGGGT ACCTCGGTTC AGATGTGTCA   1560

TCTTCCCCGA GAAAGAGTGC AGTGGCCTCA GTGATGTACA CGGTGGTCAC CCCCATGCTG   1620

AACCCCTTCA TGTACAGCCT GAGAAACAGG GATATGAAAA GTGTCCTGCG GCGGCCGCAC   1680

GGCAGCACAG TCTAATCTCA ATATCTTCTT ATCTGTTCCA TTCCTTTTGT AGTGTGGGTT   1740

AAAAAAGGCA GCAAGATCAA ATAAGATTGA CTCAGGACC TGAACACTCA TGTTTGTATA   1800

CGACCGACAA GTAGTCCCCG GAGGCCCG                                     1828
```

(2) INFORMATION FOR SEQ ID NO:3:

(i) SEQUENCE CHARACTERISTICS:
        (A) LENGTH: 358 amino acids
        (B) TYPE: amino acid
        (C) STRANDEDNESS: single
        (D) TOPOLOGY: linear (vii) IMMEDIATE SOURCE:
        (A) LIBRARY: PROSTUT09
        (B) CLONE: 1650519

(xi) SEQUENCE DESCRIPTION: SEQ ID NO:3:

```
Met Gly Phe Asn Leu Thr Leu Ala Lys Leu Pro Asn Asn Glu Leu His
 1               5                  10                  15

Gly Gln Glu Ser His Asn Ser Gly Asn Arg Ser Asp Gly Pro Gly Lys
            20                  25                  30

Asn Thr Thr Leu His Asn Glu Phe Asp Thr Ile Val Leu Pro Val Leu
        35                  40                  45

Tyr Leu Ile Ile Phe Val Ala Ser Ile Leu Leu Asn Gly Leu Ala Val
    50                  55                  60
```

-continued

```
Trp Ile Phe Phe His Ile Arg Asn Lys Thr Ser Phe Ile Phe Tyr Leu
 65                  70                  75                  80

Lys Asn Ile Val Val Ala Asp Leu Ile Met Thr Leu Thr Phe Pro Phe
                 85                  90                  95

Arg Ile Val His Asp Ala Gly Phe Gly Pro Trp Tyr Phe Lys Phe Ile
                100                 105                 110

Leu Cys Arg Tyr Thr Ser Val Leu Phe Tyr Ala Asn Met Tyr Thr Ser
            115                 120                 125

Ile Val Phe Leu Gly Leu Ile Ser Ile Asp Arg Tyr Leu Lys Val Val
        130                 135                 140

Lys Pro Phe Gly Asp Ser Arg Met Tyr Ser Ile Thr Phe Thr Lys Val
145                 150                 155                 160

Leu Ser Val Cys Val Trp Val Ile Met Ala Val Leu Ser Leu Pro Asn
                165                 170                 175

Ile Ile Leu Thr Asn Gly Gln Pro Thr Glu Asp Asn Ile His Asp Cys
            180                 185                 190

Ser Lys Leu Lys Ser Pro Leu Gly Val Lys Trp His Thr Ala Val Thr
        195                 200                 205

Tyr Val Asn Ser Cys Leu Phe Val Ala Val Leu Val Ile Leu Ile Gly
210                 215                 220

Cys Tyr Ile Ala Ile Ser Arg Tyr Ile His Lys Ser Ser Arg Gln Phe
225                 230                 235                 240

Ile Ser Gln Ser Ser Arg Lys Arg Lys His Asn Gln Ser Ile Arg Val
                245                 250                 255

Val Val Ala Val Tyr Phe Thr Cys Phe Leu Pro Tyr His Leu Cys Arg
                260                 265                 270

Met Pro Ser Thr Phe Ser His Leu Asp Arg Leu Leu Asp Glu Ser Ala
            275                 280                 285

Gln Lys Ile Leu Tyr Tyr Cys Lys Glu Ile Thr Leu Phe Leu Ser Ala
        290                 295                 300

Cys Asn Val Cys Leu Asp Pro Ile Ile Tyr Phe Phe Met Cys Arg Ser
305                 310                 315                 320

Phe Ser Arg Trp Leu Phe Lys Lys Ser Asn Ile Arg Pro Arg Ser Glu
                325                 330                 335

Ser Ile Arg Ser Leu Gln Ser Val Arg Arg Ser Glu Val Arg Ile Tyr
            340                 345                 350

Tyr Asp Tyr Thr Asp Val
        355
```

(2) INFORMATION FOR SEQ ID NO:4:

(i) SEQUENCE CHARACTERISTICS:
        (A) LENGTH: 1444 base pairs
        (B) TYPE: nucleic acid
        (C) STRANDEDNESS: single
        (D) TOPOLOGY: linear (vii) IMMEDIATE SOURCE:
        (A) LIBRARY: PROSTUT09
        (B) CLONE: 1650519

(xi) SEQUENCE DESCRIPTION: SEQ ID NO:4:

```
GGAGAATTTG AAAGGGTGCC CCAAAGGACA ATCTCTAAAG GGGTAAGGGG GATACCTACC      60

TTGTCTGGTA GGGGAGATGT TTCGTTTTCA TGCTTTACCA GAAAATCCAC TTCCCTGCCG     120

ACCTTAGTTT CAAAGCTTAT TCTTAATTAG AGACAAGAAA CCTGTTTCAA CTTGAAGACA     180
```

-continued

```
CCGTATGAGG TGAATGGACA GCCAGCCACC ACAATGAAAG AAATCAAACC AGGAATAACC    240

TATGCTGAAC CCACGCCTCA ATCGTCCCCA AGTGTTTCCT GACACGCATC TTTGCTTACA    300

GTGCATCACA ACTGAAGAAT GGGGTTCAAC TTGACGCTTG CAAAATTACC AAATAACGAG    360

CTGCACGGCC AAGAGAGTCA CAATTCAGGC AACAGGAGCG ACGGGCCAGG AAAGAACACC    420

ACCCTTCACA ATGAATTTGA CACAATTGTC TTGCCGGTGC TTTATCTCAT TATATTTGTG    480

GCAAGCATCT TGCTGAATGG TTTAGCAGTG TGGATCTTCT TCCACATTAG GAATAAAACC    540

AGCTTCATAT TCTATCTCAA AAACATAGTG GTTGCAGACC TCATAATGAC GCTGACATTT    600

CCATTTCGAA TAGTCCATGA TGCAGGATTT GGACCTTGGT ACTTCAAGTT TATTCTCTGC    660

AGATACACTT CAGTTTTGTT TTATGCAAAC ATGTATACTT CCATCGTGTT CCTTGGGCTG    720

ATAAGCATTG ATCGCTATCT GAAGGTGGTC AAGCCATTTG GGACTCTCG GATGTACAGC    780

ATAACCTTCA CGAAGGTTTT ATCTGTTTGT GTTTGGGTGA TCATGGCTGT TTTGTCTTTG    840

CCAAACATCA TCCTGACAAA TGGTCAGCCA ACAGAGGACA ATATCCATGA CTGCTCAAAA    900

CTTAAAAGTC CTTTGGGGGT CAAATGGCAT ACGGCAGTCA CCTATGTGAA CAGCTGCTTG    960

TTTGTGGCCG TGCTGGTGAT TCTGATCGGA TGTTACATAG CCATATCCAG GTACATCCAC   1020

AAATCCAGCA GGCAATTCAT AAGTCAGTCA AGCCGAAAGC GAAAACATAA CCAGAGCATC   1080

AGGGTTGTTG TGGCTGTGTA TTTTACCTGC TTTCTACCAT ATCACTTGTG CAGAATGCCT   1140

TCTACTTTTA GTCACTTAGA CAGGCTTTTA GATGAATCTG CACAAAAAAT CCTATATTAC   1200

TGCAAAGAAA TTACACTTTT CTTGTCTGCG TGTAATGTTT GCCTGGATCC AATAATTTAC   1260

TTTTTCATGT GTAGGTCATT TTCAAGATGG CTGTTCAAAA AATCAAATAT CAGACCCAGG   1320

AGTGAAAGCA TCAGATCACT GCAAAGTGTG AGAAGATCGG AAGTTCGCAT ATATTATGAT   1380

TACACTGATG TGTAGGCCTT TTATTGTTTG TTGGAATCGA TATGTACAAA GTGTAATACA   1440

TCAG                                                                1444
```

(2) INFORMATION FOR SEQ ID NO:5:

(i) SEQUENCE CHARACTERISTICS:
        (A) LENGTH: 309 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1314667

(xi) SEQUENCE DESCRIPTION: SEQ ID NO:5:

```
Met Glu Leu Glu Asn Asp Thr Arg Ile Pro Glu Phe Leu Leu Gly
 1               5                  10                  15

Phe Ser Glu Glu Pro Lys Leu Gln Pro Phe Leu Phe Gly Leu Phe Leu
                20                  25                  30

Ser Met Tyr Leu Val Thr Ile Leu Gly Asn Leu Leu Ile Leu Ala
        35                  40                  45

Val Ser Ser Asp Ser His Leu His Thr Pro Met Tyr Phe Phe Leu Ala
    50                  55                  60

Asn Leu Ser Phe Val Asp Ile Cys Phe Thr Cys Thr Thr Ile Pro Lys
65                  70                  75                  80

Met Leu Val Asn Ile Gln Thr Gln Arg Lys Val Ile Thr Tyr Glu Ser
                85                  90                  95
```

-continued

```
Cys Ile Ile Gln Met Tyr Phe Phe Glu Leu Phe Ala Gly Ile Asp Asn
            100                 105                 110

Phe Leu Leu Thr Val Met Ala Tyr Asp Arg Tyr Met Ala Ile Cys Tyr
        115                 120                 125

Pro Leu His Tyr Met Val Ile Met Asn Pro Gln Leu Cys Ser Leu Leu
    130                 135                 140

Leu Leu Val Ser Trp Ile Met Ser Ala Leu His Ser Leu Leu Gln Thr
145                 150                 155                 160

Leu Met Val Leu Arg Leu Ser Phe Cys Thr His Phe Gln Ile Pro His
                165                 170                 175

Phe Phe Cys Glu Leu Asn Gln Met Ile Gln Leu Ala Cys Ser Asp Thr
            180                 185                 190

Phe Leu Asn Asn Met Met Leu Tyr Phe Ala Ala Ile Leu Leu Gly Val
        195                 200                 205

Ala Pro Leu Val Gly Val Leu Tyr Ser Tyr Phe Lys Ile Val Ser Ser
    210                 215                 220

Ile Arg Gly Ile Ser Ser Ala His Ser Lys Tyr Lys Ala Phe Ser Thr
225                 230                 235                 240

Cys Ala Ser His Leu Ser Val Val Ser Leu Phe Tyr Cys Thr Ser Leu
                245                 250                 255

Gly Val Tyr Leu Ser Ser Ala Ala Pro Gln Ser Thr His Thr Ser Ser
            260                 265                 270

Val Ala Ser Val Met Tyr Thr Val Thr Pro Met Leu Asn Pro Phe
        275                 280                 285

Ile Tyr Ser Leu Arg Asn Lys Asp Ile Lys Gly Ala Leu Asn Val Phe
    290                 295                 300

Phe Arg Gly Lys Pro
305
```

(2) INFORMATION FOR SEQ ID NO:6:

(i) SEQUENCE CHARACTERISTICS:
        (A) LENGTH: 333 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 205814

(xi) SEQUENCE DESCRIPTION: SEQ ID NO:6:

```
Met Asp Ser Ser Asn Arg Thr Arg Val Ser Glu Phe Leu Leu Leu Gly
 1               5                  10                  15

Phe Val Glu Asn Lys Asp Leu Gln Pro Leu Ile Tyr Gly Leu Phe Leu
            20                  25                  30

Ser Met Tyr Leu Val Thr Val Ile Gly Asn Ile Ser Ile Ile Val Ala
        35                  40                  45

Ile Ile Ser Asp Pro Cys Leu His Thr Pro Met Tyr Phe Phe Leu Ser
    50                  55                  60

Asn Leu Ser Phe Val Asp Ile Cys Phe Ile Ser Thr Thr Val Pro Lys
65                  70                  75                  80

Met Leu Val Asn Ile Gln Thr Gln Asn Asn Val Ile Thr Tyr Ala Gly
                85                  90                  95

Cys Ile Thr Gln Ile Tyr Phe Phe Leu Leu Phe Val Glu Leu Asp Asn
            100                 105                 110
```

```
Phe Leu Leu Thr Ile Met Ala Tyr Asp Arg Tyr Val Ala Ile Cys His
        115                 120                 125

Pro Met His Tyr Thr Val Ile Met Asn Tyr Lys Leu Cys Gly Phe Leu
        130                 135                 140

Val Leu Val Ser Trp Ile Val Ser Val Leu His Ala Leu Phe Gln Ser
145                 150                 155                 160

Leu Met Met Leu Ala Leu Pro Phe Cys Thr His Leu Glu Ile Pro His
                165                 170                 175

Tyr Phe Cys Glu Pro Asn Gln Val Ile Gln Leu Thr Cys Ser Asp Ala
                180                 185                 190

Phe Leu Asn Asp Leu Val Ile Tyr Phe Thr Leu Val Leu Leu Ala Thr
        195                 200                 205

Val Pro Leu Ala Gly Ile Phe Tyr Ser Tyr Phe Lys Ile Val Ser Ser
210                 215                 220

Ile Cys Ala Ile Ser Ser Val His Gly Lys Tyr Lys Ala Phe Ser Thr
225                 230                 235                 240

Cys Ala Ser His Leu Ser Val Val Ser Leu Phe Tyr Cys Thr Gly Leu
                245                 250                 255

Gly Val Tyr Leu Ser Ser Ala Ala Asn Asn Ser Ser Gln Ala Ser Ala
                260                 265                 270

Thr Ala Ser Val Met Tyr Thr Val Thr Pro Met Val Asn Pro Phe
        275                 280                 285

Ile Tyr Ser Leu Arg Asn Lys Asp Val Lys Ser Val Leu Lys Lys Thr
        290                 295                 300

Leu Cys Glu Glu Val Ile Arg Ser Pro Pro Ser Leu Leu His Phe Phe
305                 310                 315                 320

Leu Val Leu Cys His Leu Pro Cys Phe Ile Phe Cys Tyr
                325                 330

(2) INFORMATION FOR SEQ ID NO:7:

(i) SEQUENCE CHARACTERISTICS:
        (A) LENGTH: 314 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 32086

(xi) SEQUENCE DESCRIPTION: SEQ ID NO:7:

Met Met Gly Gln Asn Gln Thr Ser Ile Ser Asp Phe Leu Leu Leu Gly
 1                   5                  10                  15

Leu Pro Ile Gln Pro Glu Gln Gln Asn Leu Cys Tyr Ala Leu Phe Leu
                20                  25                  30

Ala Met Tyr Leu Thr Thr Leu Leu Gly Asn Leu Leu Ile Ile Val Leu
        35                  40                  45

Ile Arg Leu Asp Ser His Leu His Thr Pro Met Tyr Leu Phe Leu Ser
    50                  55                  60

Asn Leu Ser Phe Ser Asp Leu Cys Phe Ser Ser Val Thr Ile Pro Lys
65                  70                  75                  80

Leu Leu Gln Asn Met Gln Asn Gln Asp Pro Ser Ile Pro Tyr Ala Asp
                85                  90                  95

Cys Leu Thr Gln Met Tyr Phe Phe Leu Leu Phe Gly Asp Leu Glu Ser
                100                 105                 110
```

```
Phe Leu Leu Val Ala Met Ala Tyr Asp Arg Tyr Val Ala Ile Cys Phe
            115                 120                 125

Pro Leu His Tyr Thr Ala Ile Met Ser Pro Met Leu Cys Leu Ala Leu
        130                 135                 140

Val Ala Leu Ser Trp Val Leu Thr Thr Phe His Ala Met Leu His Thr
145                 150                 155                 160

Leu Leu Met Ala Arg Leu Cys Phe Cys Ala Asp Asn Val Ile Pro His
                165                 170                 175

Phe Phe Cys Asp Met Ser Ala Leu Leu Lys Leu Ala Phe Ser Asp Thr
            180                 185                 190

Arg Val Asn Glu Trp Val Ile Phe Ile Met Gly Gly Leu Ile Leu Val
        195                 200                 205

Ile Pro Phe Leu Leu Ile Leu Gly Ser Tyr Ala Arg Ile Val Ser Ser
210                 215                 220

Ile Leu Lys Val Pro Ser Ser Lys Gly Ile Cys Lys Ala Phe Ser Thr
225                 230                 235                 240

Cys Gly Ser His Leu Ser Val Val Ser Leu Phe Tyr Gly Thr Val Ile
                245                 250                 255

Gly Leu Tyr Leu Cys Ser Ser Ala Asn Ser Ser Thr Leu Lys Asp Thr
                260                 265                 270

Val Met Ala Met Met Tyr Thr Val Val Thr Pro Met Leu Asn Pro Phe
            275                 280                 285

Ile Tyr Ser Leu Arg Asn Arg Asp Met Lys Gly Ala Leu Ser Arg Val
        290                 295                 300

Ile His Gln Lys Lys Thr Phe Phe Ser Leu
305                 310
```

(2) INFORMATION FOR SEQ ID NO:8:

(i) SEQUENCE CHARACTERISTICS:
        (A) LENGTH: 338 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 285995

(xi) SEQUENCE DESCRIPTION: SEQ ID NO:8:

```
Met Ile Asn Ser Thr Ser Thr Gln Pro Pro Asp Glu Ser Cys Ser Gln
1               5                   10                  15

Asn Leu Leu Ile Thr Gln Gln Ile Ile Pro Val Leu Tyr Cys Met Val
                20                  25                  30

Phe Ile Ala Gly Ile Leu Leu Asn Gly Val Ser Gly Trp Ile Phe Phe
            35                  40                  45

Tyr Val Pro Ser Ser Lys Ser Phe Ile Ile Tyr Leu Lys Asn Ile Val
        50                  55                  60

Ile Ala Asp Phe Val Met Ser Leu Thr Phe Pro Phe Lys Ile Leu Gly
65                  70                  75                  80

Asp Ser Gly Leu Gly Pro Trp Gln Leu Asn Val Phe Val Cys Arg Val
                85                  90                  95

Ser Ala Val Leu Phe Tyr Val Asn Met Tyr Val Ser Ile Val Phe Phe
                100                 105                 110

Gly Leu Ile Ser Phe Asp Arg Tyr Tyr Lys Ile Val Lys Pro Leu Trp
            115                 120                 125
```

```
Thr Ser Phe Ile Gln Ser Val Ser Tyr Ser Lys Leu Leu Ser Val Ile
    130                 135                 140

Val Trp Met Leu Met Leu Leu Ala Val Pro Asn Ile Ile Leu Thr
145                 150                 155                 160

Asn Gln Ser Val Arg Glu Val Thr Gln Ile Lys Cys Ile Glu Leu Lys
                165                 170                 175

Ser Glu Leu Gly Arg Lys Trp His Lys Ala Ser Asn Tyr Ile Phe Val
                180                 185                 190

Ala Ile Phe Trp Ile Val Phe Leu Leu Ile Val Phe Tyr Thr Ala
            195                 200                 205

Ile Thr Lys Lys Ile Phe Lys Ser His Leu Lys Ser Ser Arg Asn Ser
    210                 215                 220

Thr Ser Val Lys Lys Ser Ser Arg Asn Ile Phe Ser Ile Val Phe
225                 230                 235                 240

Val Phe Phe Val Cys Phe Val Pro Tyr His Ile Ala Arg Ile Pro Tyr
                245                 250                 255

Thr Lys Ser Gln Thr Glu Ala His Tyr Ser Cys Gln Ser Lys Glu Ile
                260                 265                 270

Leu Arg Tyr Met Lys Glu Phe Thr Leu Leu Leu Ser Ala Ala Asn Val
        275                 280                 285

Cys Leu Asp Pro Ile Ile Tyr Phe Phe Leu Cys Gln Pro Phe Arg Glu
    290                 295                 300

Ile Leu Cys Lys Lys Leu His Ile Pro Leu Lys Ala Gln Asn Asp Leu
305                 310                 315                 320

Asp Ile Ser Arg Ile Lys Arg Gly Asn Thr Thr Leu Glu Ser Thr Asp
                325                 330                 335

Thr Leu (2) INFORMATION FOR SEQ ID NO:9:

(i) SEQUENCE CHARACTERISTICS:
        (A) LENGTH: 342 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 49443

(xi) SEQUENCE DESCRIPTION: SEQ ID NO:9:

Met Glu Leu Asn Ser Ser Arg Val Asp Ser Glu Phe Arg Tyr Thr
1               5                   10                  15

Leu Phe Pro Ile Val Tyr Ser Ile Ile Phe Val Leu Gly Ile Ile Ala
                20                  25                  30

Asn Gly Tyr Val Leu Trp Val Phe Ala Arg Leu Tyr Pro Ser Lys Lys
            35                  40                  45

Leu Asn Glu Ile Lys Ile Phe Met Val Asn Leu Thr Val Ala Asp Leu
    50                  55                  60

Leu Phe Leu Ile Thr Leu Pro Leu Trp Ile Val Tyr Tyr Ser Asn Gln
65                  70                  75                  80

Gly Asn Trp Phe Leu Pro Lys Phe Leu Cys Asn Leu Ala Gly Cys Leu
                85                  90                  95

Phe Phe Ile Asn Thr Tyr Cys Ser Val Ala Phe Leu Gly Val Ile Thr
                100                 105                 110
```

-continued

```
Tyr Asn Arg Phe Gln Ala Val Lys Tyr Pro Ile Lys Thr Ala Gln Ala
        115                 120                 125

Thr Thr Arg Lys Arg Gly Ile Ala Leu Ser Leu Val Ile Trp Val Ala
        130                 135                 140

Ile Val Ala Ala Ala Ser Tyr Phe Leu Val Met Asp Ser Thr Asn Val
145                 150                 155                 160

Val Ser Asn Lys Ala Gly Ser Gly Asn Ile Thr Arg Cys Phe Glu His
                165                 170                 175

Tyr Glu Lys Gly Ser Lys Pro Val Leu Ile Ile His Ile Cys Ile Val
                180                 185                 190

Leu Gly Phe Phe Ile Val Phe Leu Leu Ile Leu Phe Cys Asn Leu Val
            195                 200                 205

Ile Ile His Thr Leu Leu Arg Gln Pro Val Lys Gln Gln Arg Asn Ala
    210                 215                 220

Glu Val Arg Arg Arg Ala Leu Trp Met Val Cys Thr Val Leu Ala Val
225                 230                 235                 240

Phe Val Ile Cys Phe Val Pro His His Met Val Gln Leu Pro Trp Thr
                245                 250                 255

Leu Ala Glu Leu Gly Met Trp Pro Ser Ser Asn His Gln Ala Ile Asn
            260                 265                 270

Asp Ala His Gln Val Thr Leu Cys Leu Leu Ser Thr Asn Cys Val Leu
        275                 280                 285

Asp Pro Val Ile Tyr Cys Phe Leu Thr Lys Lys Phe Arg Lys His Leu
        290                 295                 300

Ser Glu Lys Leu Asn Ile Met Arg Ser Ser Gln Lys Cys Ser Arg Val
305                 310                 315                 320

Thr Thr Asp Thr Gly Thr Glu Met Ala Ile Pro Ile Asn His Thr Pro
                325                 330                 335

Val Asn Pro Ile Lys Asn
            340
```